US006207148B1

(12) United States Patent
Bandman et al.

(10) Patent No.: US 6,207,148 B1
(45) Date of Patent: Mar. 27, 2001

(54) DISEASE ASSOCIATED PROTEIN KINASES

(75) Inventors: Olga Bandman; Jennifer L. Hillman; Neil C. Corley, all of Mountain View; Karl J. Guegler, Menlo Park; Preeti Lal, Santa Clara; Surya K. Goli; Purvi Shah, both of Sunnyvale, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/272,796

(22) Filed: Mar. 19, 1999

Related U.S. Application Data

(62) Division of application No. 08/878,989, filed on Jun. 19, 1997, now Pat. No. 5,885,803.

(51) Int. Cl.[7] .............................. A61K 38/43; C12N 9/00; G01N 33/53; C07K 14/00
(52) U.S. Cl. ........................ 424/94.1; 435/183; 435/7.71; 435/7.72; 530/350
(58) Field of Search ........................... 530/350; 435/183, 435/7.71, 7.72; 424/94.1

(56) References Cited

U.S. PATENT DOCUMENTS

| 5,663,314 | * | 9/1997 | Seger et al. ........................... 536/23.2 |
| 5,981,205 | * | 11/1999 | Hemmings et al. .................... 435/15 |

FOREIGN PATENT DOCUMENTS

| 43 29 177 | * | 3/1995 | (DE) . |
| WO 97 10365 | | 4/1995 | (WO) . |
| WO 95 14772 | | 6/1995 | (WO) . |
| WO 96 36642 | | 11/1996 | (WO) . |

OTHER PUBLICATIONS

Hardie, G., et al., "The Eukaryotic Protein Kinase Superfamily", *The Protein Kinase Facts Book*, 1:7–20 (1995).
Isselbacher, K.J., et al., "Adrenergic Receptors", *Harrison's Principles of Internal Medicine*, 1:416–431, 1887 (1994).
Haribabu, B., et al., "Human calcium–calmodulin dependent protein kinase I: cDNA cloning, domain structure and activation by phosphorylation at threonine–177 by calcium–calmodulin dependent protein kinase I kinase", *The EMBO Journal*, 14:3679–3686 (1995).
Gao, G., et al., "Non–catalytic β– and γ–Subunit Isoforms of the 5'–AMP–activated Protein Kinase", *The Journal of Biological Chemistry*, 271(15):8675–8681 (1996).
Egan, S.E., et al., "The pathway to signal achievement", *Nature*, 365:781–783 (1993).
Li, B., et al., "prk, a Cytokine–inducible Human Protein Serine/Threonine Kinase whose Expression appears to be Down–regulated in Lung Carcinomas", *J. Biol. Chem.*, 271:19402–19408 (1996).
Carbonneau, H., et al., "1002 Protein Phosphatases?, " *Annu. Rev. Cell Biol.*, 8:463–93 (1992).

Davie, J.R., et al., "Expression and Characterization of Branched–chain α–Ketoacid Dehydrogenase Kinase from the Rat", *The Journal of Biological Chemistry*, 270(34):19861–19867 (1995).
Nezu, J., (GI 1827450) GenBank Sequence Dataase (Accession 1827450), National Center for Biotechnology Information: National Library of Medicine, Bethesda, Maryland 20849.
Otsu, M., et al., "Isolatien of two members of the rat MAP kinase kinase gene family", *FEBS Letters*, 320(3):246–250 (1993).(GI 303804).
Millward, T., et al., "Molecular cloning and characterization of a conserved nuclear serine (threonine) protein kinase", *Proc. Natl. Acad. Sci. USA*, 92:5022–5026 (1995).(GI 854170).
Nezu, J., (GI 1827452) GenBank Sequence Database (Accession AB000450), National Center for Biotechnology Information: National Library of Medicine, Bethesda, Maryland 20849.
Nezu, J., et al., (GI 1827449) GenBank Sequence Database (Accession AB000449), National Center for Biotechnology Information: National Library of Medicine, Bethesda, Maryland 20849.
Otsu, M., et al., (GI 303804) GenBank Sequence Database (Accession D14592), National Center for Biotechnology Information: National Library of Medicine, Bethesda, Maryland 20849.
Otsu, M., et al., (GI 286229) GenBank Sequence Database (Accession D14592), National Center for Biotechnology Information: National Library of Medicine, Bethesda, Maryland 20849.
Millward, T., (GI 854170) GenBank Sequence Database (Accession Z35102), National Center for Biotechnology Information: National Library of Medicine, Bethesda, Maryland 20849.
Millward, T.,(GI 854169) GenBank Sequence Database (Accession Z35102), National Center for Biotechnology Information: National Library of Medicine, Bethesda, Maryland 20849.
Haribabu, B., et al., (GI 790790) GenBank Sequence Database (Accession L41816), National Center for Biotechnology Information: National Library of Medicine, Bethesda, Maryland 20849.
Haribabu, B., et al. (GI 790789) GenBank Sequence Database (Accession L41816), National Center for Biotechnology Information: National Library of Medicine, Bethesda, Maryland 20849.

(List continued on next page.)

*Primary Examiner*—Karen Cochrane Carlson
(74) *Attorney, Agent, or Firm*—Incyte Genomics, Inc.

(57) ABSTRACT

The invention provides human disease associated protein kinases and polynucleotides (collectively designated DAPK) which identify and encode them. The invention also provides expression vectors, host cells, agonists, antibodies and antagonists. The invention further provides methods for diagnosing and treating disorders associated with expression of human disease associated protein kinases.

7 Claims, 15 Drawing Sheets

OTHER PUBLICATIONS

Popov, K.M., et al., (GI 924921) GenBank Sequence Database (Accession U27456), National Library of Medicine, Bethesda, Maryland 20849.

Popov, K.M., et al., (GI 924920) GenBank Sequence Database (Accession U27456), National Center for Biotechnology Information: National Center for Biotechnology Information: National Library of Medicine, Bethesda, Maryland 20849.

Gao, G., et al., (GI 1335856) GenBank Sequence Database (Accession U42412), National Center for Biotechnology Information: National Library of Medicine, Bethesda, Maryland 20849.

Gao, G., et al., (GI 1335855) GenBank Sequence Database (Accession U42412), National Center for Biotechnology Information: National Library of Medicine, Bethesda, Maryland 20849.

Ouyang, B., "Human Serum–Inducible Kinase mRNA, complete cds", EMBL Database, Apr. 27, 1998, Accession Nr. AF059617.

Lake, R.J. and W.R. Jelinek, "Cell cycle and terminal differentiation–associated regulation of the mouse mRNA encoding a conserved mitotic protein kinase", *Molecular and Cellular Biology*, 13: 7793–7801 (1993).

Goldsteyn, R.M. et al., "Cell cycle analysis and chromosomal localization of humal plk1, a putative homologue of thr mitotic kinases Drosophila polo and Saccharomyces Cdc5", *Journal of Cell Science*, 107: 1509–1517 (1994).

Hamanaka, R. et al., "Cloning and characterization of human and murine homologues of the Drosophila polo Serine–Threonine Kinase", *Cell Growth and Differentiation*, 5: 249–257 (1994).

Goebel et al., 1990; Virology 179:247–266.*

Popov et al., 1992; J. Biol. Chem. 267:13127–13130.*

Stapleton et al., 1994; J. Biol. Chem. 269:29343–29346.*

Picciotto et al., 1993; J. Biol. Chem. 268:26512–26521.*

Yokokura et al., Mar. 7, 1997; Biochim. Biophys. Acta. 1338:8–12.*

* cited by examiner

```
  1  M E L L R T I T Y Q P A A S T K M C E Q A L G K G C G A D S K K K R P P Q P P E   DAPK-1
  1  M - - - - - - - - - - - - - - - - - - - - - - - - - - - - - - - - - - - - - - -   g1488263

41  E S Q P P Q S Q A Q V P P A A P H H H H H S H S G P E I S R I I V D P T T G K     DAPK-1
  2  - - - - - - - - L A G L P T S D P - - - - - - - - - - G R L I T D P R S G R       g1488263

81  R Y C R G K V L G K G G F A K C Y E M T D L T N N K V Y A A K I I P H S R V A K   DAPK-1
 22  T Y L K G R L L G K G G F A R C Y E A T D T E T G S A Y A V K V I P Q S R V A K   g1488263

121  P H Q R E K I D K E I E L H R I L H H K H V V Q F Y H Y F E D K E N I Y I L L E   DAPK-1
 62  P H Q R E K I L N E I E L H R D L Q H R H I V R F S H H F E D A D N I Y I F L E   g1488263

161  Y C S R R S M A H I L K A R K V L T E P E V R Y Y L R Q I V S G L K Y L H E Q E   DAPK-1
102  L C S R K S L A H I W K A R H T L L E P E V R Y Y L R Q I L S G L K Y L H Q R G   g1488263

201  I L H R D L K L G N F F I N E A M E L K V G D F G L A A R L E P L E H R R T I     DAPK-1
142  I L H R D L K L G N F F I T E N M E L K V G D F G L A A R L E P P E Q R K K T I   g1488263
```

FIGURE 1A

```
241  C G T P N Y L S P E V L N K Q G H G C E S D I W A L G C V M Y T M L L G R P P F   DAPK-1
182  C G T P N Y V A P E V L L R Q G H G P E A D V W S L G C V M Y T L L C G S P P F   gI488263

281  E T T N L K E T Y R C I R E A R Y T M P S S L L A P A K H L I A S M L S K N P E   DAPK-1
222  E T A D L K E T Y R C I K Q V H Y T L P A S L P A R Q L L A A I L R A S P R     gI488263

321  D R P S L D D I I R H D F F L Q G F T P D R L S S C C H T V P D F H L S S P A   DAPK-1
262  D R P S I D Q I L R H D F F T K G Y T P D R L P I S C V T V P D L T P P N P A   gI488263

361  K N F F K K A A A A L F G G K K D K A R Y I D T H N R V S K E D E D I Y K L R H   DAPK-1
302  R S L F A K V T K S L F G R K K K S K N H - - - - A Q E R D E V S G L V S       gI488263

401  D L K K T S I T Q Q P S K H R T D E E L Q P P T T V A R S G T P A V E N K Q Q   DAPK-1
335  G L M R T S V G H Q D A R P E A P A A S G P A P V S L - - - - - V E T A P E     gI488263

441  I G D A I R M I V R G T L G S C S S S E C L E D S T M G S V A D T V A R V L R   DAPK-1
368  D S S P - - - - R G T L A S G D G F E - - E G L T V A T V V E S A L C A L R     gI488263
```

FIGURE 1B

```
481 G C L E N M P E A D C I P K E - Q L S T S F Q W V T K W V D Y S N K Y G F G Y Q    DAPK-1
401 N C I A F M P P A E Q N P A P L A Q P E P L V W V S K W V D Y S N K F G F G Y Q    g1488263

520 L S D H T V G V L F N N G A H M S L L P D K K T A H Y Y A E L G Q C S V F P A T    DAPK-1
441 L S S R R V A V L F N D G T H M A L S A N R K T V H Y N P T S T K H F S F S V G    g1488263

560 D A P E Q F I S Q V T V L K Y F S H Y M E E N L M D G G D L P S V T D I R R P -    DAPK-1
481 A V P R A L Q P Q L G I L R Y F A S Y M E Q H L M K G G D L P S V E E V E V P A    g1488263

599 R L Y L L Q W L K S D K A L M M L F N D G T F Q V N F Y H D H T K L I I C S Q N    DAPK-1
521 P P L L Q W V K T D Q A L L M L F S D G T V Q V N F Y G D H T K L I L S G - W    g1488263

639 E E Y L L T Y I N E D R I S T F R L T T L L M S G C S S E L K N R M E Y A L N    DAPK-1
560 E P L L V T F V A R N R S A C T Y L A S H L R Q L G C S P D L R Q R L R Y A L R    g1488263

679 M L L Q R C - N                                                                    DAPK-1
600 L L R D R S P A                                                                    g1488263
```

FIGURE 1C

```
  1                              -NEKYKLPIPFPEGKVLDDMEGNQWVLG   DAPK-2
  1   MPRVKAAQAGRQSSAKRHLAEQFAVGEITTDMAKKEWKVG                  gi1827450

33   KKIGSGGFGLIYLA--FPTNKPEKDARHVVKVEYQENGPL                  DAPK-2
 41   LPIGQGGFGCIYLADMNSSESVGSDAPCVVKVEPSDNGPL                  gi1827450

71   FSELKFYQRVAKKDCIKKWIERKQLDYLGIPLFYGSGLTE                  DAPK-2
 81   FTELKFYQRAAKPEQIQKWIRTRKLKYLGVPKYWGSGLHD                  gi1827450

111   FKGRSYRFMVERLGIDLQKISGQNGT-FKKSTVLQLGIR                   DAPK-2
121   KNGKSYRFMIMDRFGSDLQKIYEANAKRFSRKTVLQLSLR                  gi1827450

150   MLDVLEYIHENEYVHGDVKAANLLLGYKNPDQVYLADYGL                  DAPK-2
161   ILDILEYIHEHEYVHGDIKASNLLLNYKNPDQVYLVDYGL                  gi1827450

190   SYRYCPNGNHKQYQENPRKGHNGTIEFTSLDAHKGVGEIA                  DAPK-2
201   AYRYCPEGVHKKEYKEDPKRCHDGTIEFTSIDAHNGVAP--                 gi1827450
```

FIGURE 2A

```
230 Q F L V C A H S L A Y D E K P N Y Q A L K K I L N P H G I P L G P L D F S T K G    DAPK-2
239 - - - - - - - - - - - - - - - - - - - - - - - - - S R R G - D L E I L G Y C - M I   g1827450

270 Q S I N V H T P N S Q K V D S Q K A A T K Q V N K A H N R L I E K K V H S E R S    DAPK-2
253 Q W L T G H L P W E D N L K D P K Y V R D S - - - - - - - - - - - - -              g1827450

310 A E S C A T W K V Q K E E K L I G L M N N E A A Q E S T R - R R Q K Y Q E S Q E    DAPK-2
275 - - - - - - - - K I R Y R E N I A S L M D K C F P E K N K P G E I A K Y M E T V K  g1827450

349 P L N E V N S F P Q K I S Y T Q F P N S F Y E P H Q D F T S P D I F K - - - K S     DAPK-2
308 L L D - - - Y T E K P L Y E N L R D I L L Q G L K A I G S K D D G K L D L S V       g1827450

386 R S P S W Y K Y T S T V S T G I T D L E S S T G L W P T I S Q F T L S E E T N A    DAPK-2
344 V E N G G L K A K T I T K K R K K E I E E S K E - - P G V E D T E W S N T Q T E    g1827450

426 D V Y Y Y R I I I P V L L M L V F L A L F F L                                      DAPK-2
382 E A I Q T R S R T R K R V Q K                                                     g1827450
```

FIGURE 2B

|     | DAPK-3 | g303804 |
|-----|--------|---------|
| 1   | M L A R R K P V L P A L T I N P T I A E G P S P T S E G A S E A N L V D L Q K K | |
| 1   | M L A R R K P V L P A L T I N P T I A E G P S P T S E G A S E A H L V D L Q K K | |
| 41  | L E E L E L D E Q Q K K R L E A F L T Q K A K V G E L K D D D F E R I S E L G A | |
| 41  | L E E L D L D E Q Q R K R L E A F L T Q K A K V G E L K D D D F E R I S E L G A | |
| 81  | G N G G V V T K V Q H R P S G L I M A R K L I H L E I K P A I R N Q I I R E L Q | |
| 81  | G N G G V V T K A R H R P S G L I M A R K L I H L E I K P A V R N Q I I R E L Q | |
| 121 | V L H E C N S P Y I V G F Y G A F Y S D G E I S I C M E H M D G G S L D H L L K | |
| 121 | V L H E C N S P Y I V G F Y G A F Y S D G E I S I C M E H M D G G S L D Q V L K | |
| 161 | E A K R I P E E I L G K V S I A V L R G L A Y L R E K H Q I M H R D V K P S N I | |
| 161 | E A K R I P E D I L G K V S I A V L R G L A Y L R E K H Q I M H R D V K P S N I | |

FIGURE 3A

```
201  L V N S R G E I K L C D F G V S G Q L I D S M A N S F V G T R S Y M A P E R L Q   DAPK-3
201  L V N S R G E I K L C D F G V S G Q L I D S M A N S F V G T R S Y M S P E R L Q   g303804

241  G T H Y S V Q S D I W S M G L S L V E L A V G R Y P I P P P D A K E L E A I F G   DAPK-3
241  G T H Y S V Q S D I W S M G L S L V E L A I G R Y P I P P P D A K E L E A S F G   g303804

281  R P V V D G E E G E P H S I S P R P R P P G R P V S G H G M D S R P A M A I F E   DAPK-3
281  R P V V D G A D G E P H S V S P R P R P P G R P I S G H G M D S R P A M A I F E   g303804

321  L L D Y I V N E P P P K L P N G V F T P D F Q E F V N K C L I K N P A E R A D L   DAPK-3
321  L L D Y I V N E P P P K L P S G V F S S D F Q E F V N K C L I K N P A E R A D L   g303804

361  K M L T N H T F I K R S E V E E V D F A G W L C K T L R L N Q P G T P T R T A V   DAPK-3
361  K L L T N H A F I K R S E G E D V D F A G W L C R T L R L K Q P S T P T R T A V   g303804
```

FIGURE 3B

```
  1 MAMTAGTTTFPMSNHTRERVTVAKLTLENFYSNLILQHE    DAPK-4
  1 MAMT-GSTPCSSMSNHTKERVTMTKVTLENFYSNLIAQHE    g854170

41 ERETRQKKLEVAMEEEGLADEEKKLRRSQHARKETEFLRL    DAPK-4
 40 EREMRQKKLEKVMEEEGLKDEEKRLRRSAHARKETEFLRL    g854170

81 KRTRLGLDDFESLKVIGRGAFGEVRLVHKKDTGHIYAMKI    DAPK-4
 80 KRTRLGLEDFESLKVIGRGAFGEVRLVQKKDTGHVYAMKI    g854170

121 LRKSDMLEKEQVAHIRAERDILVEADGAWVVKMFYSFQDK    DAPK-4
120 LRKADMLEKEQVGHIRAERDILVEADSLWVVKMFYSFQDK    g854170

161 RNLYLIMEFLPGGDMMTLLMKKDTLTEEETQFYISETVLA    DAPK-4
160 LNLYLIMEFLPGGDMMTLLMKKDTLTEEETQFYIAETVLA    g854170

201 IDAIHQLGFIHRDIKPDNLLLDAKGHVKLSDFGSCTGLKK    DAPK-4
200 IDSIHQLGFIHRDIKPDNLLLDSKGHVKLSDFGLCTGLKK    g854170
```

FIGURE 4A

| 241 | AHRTEFFYRNLTHNPPSDFSFQNMNSKRRKAETWKKNRRQLA | DAPK-4 |
| 240 | AHRTEFFYRNLNHSLPSDFTFQNMNSKRRKAETWKRNRRQLA | g854170 |

| 281 | YSTVGTPDYIAPEVFMQTGYNKLCDWWSLGVIMYEMLIGY | DAPK-4 |
| 280 | FSTVGTPDYIAPEVFMQTGYNKLCDWWSLGVIMYEMLIGY | g854170 |

| 321 | PPFCSETPQETYRKVMNWKETLVFPPEVPISEKAKDLILR | DAPK-4 |
| 320 | PPFCSETPQETYKKVMNWKETLTFPPEVPISEKAKDLILR | g854170 |

| 361 | FCIDSENRIGNSGVEEIKGHPFFEGVDWEHIRERPAAIPI | DAPK-4 |
| 360 | FCCEWEHRIGAPGVEEIKSNSFFEGVDWEHIRERPAAISI | g854170 |

| 401 | EIKSIDDTSNFDDFPESDILQPVPNTT---EPDYKSKDWV | DAPK-4 |
| 400 | EIKSIDDTSNFDEFPESDILKPTVATSNHPETDYKNKDWV | g854170 |

| 438 | FLNYTYKRFEGLTQRGSIPTYMKAGKL | DAPK-4 |
| 440 | FINYTYKRFEGLTARGAIPSYMKAAK | g854170 |

FIGURE 4B

```
  1   MLLK----KHTEDISSVYEIRERLGSGAFSEVVLAQER     DAPK-5
  1   MLGAVEGPRWKQAEDIRDIYDFRDVLGTGAFSEVILAEDK   g790790

36   GSAHLVALKCIPKKALRGKEALVENEIAVLRRISHPNIVA    DAPK-5
 41   RTQKLVAIKCIAKEALEGKEGSMENEIAVLHKIKHPNIVA   g790790

76   LEDVHESPSHLYLAMELVTGGELFDRIMERGSYTEKDASH    DAPK-5
 81   LDDIYESGGHLYLIMQLVSGGELFDRIVEKGFYTERDASR   g790790

116   LVGQVLGAVSYLHSLGIVHRDLKPENLLYATPFEDSKIMV    DAPK-5
121   LIFQVLDAVKYLHDLGIVHRDLKPENLLYSLDEDSKIMI   g790790

156   SDFGLSKIQ-AGNMLGTACGTPGYVAPELLEQKPYGKAVD    DAPK-5
161   SDFGLSKMEDPGSVLSTACGTPGYVAPEVLAQKPYSKAVD   g790790

195   VWALGVISYILLCGYPPFYDESDPELFSQILRASYEFFDXP   DAPK-5
201   CWSIGVIAYILLCGYPPFYDENDAKLFEQILKAEYEFDSP   g790790
```

FIGURE 5A

```
235 FWDDISESGKDFIRHLLERDLQKRFTCQQALRDLWIFWDT    DAPK-5
241 YWDDISDSAKDFIRHLMEKDPEKRFTCEQALQHPWIAGDT    g790790

275 GFGRDILGFVSEQIRKNFAWTHWKRAFNATLFLRHIRKKL-   DAPK-5
281 ALDKNIHQSVSEQIKKNFAKSKWKQAFNATAVVRHMRKKLQ   g790790

314 -GQIPEGEG--ASEQGMXRHSHXG----------------   DAPK-5
321 LGTSQEGQQTASHGELLTPVAGGPAAGCCCRDCCVEPGT     g790790

335 -LRAGQPPKW                                  DAPK-5
361 ELSPTLPHQL                                  g790790
```

FIGURE 5B

```
  1  M I L A S V L R S G P G G G L P L P L R P L L G P A L A L R A R S T S A T D T H H V   DAPK-6
  1  - - - - - - - - - - - - - - - - - - - - - - - - - - - - - - S T S A T D T H H V   g924921

41  E M A R E R S K T V T S F Y N Q S A I D A A A E K P S V R L T P T M M L Y A G R   DAPK-6
 11  E L A R E R S K T V T S F Y N Q S A I D V V A E K P S V R L T P T M M L Y S G R   g924921

81  S Q D G S H L L K S A R Y L Q Q E L P V R I A H R I K G F R C L P F I I G C N P   DAPK-6
 51  S Q D G S H L L K S G R Y L Q Q E L P V R I A H R I K G F R S L P F I I G C N P   g924921

121  T I L H V H E L Y I R A F Q K L T D F P P I K D Q A D E A Q Y C Q L V R Q L L D   DAPK-6
 91  T I L H V H E L Y I R A F Q K L T D F P P I K D Q A D E A Q Y C Q L V R Q L L D   g924921

161  D H K D V V T L L A E G L R E S R K H I E D E K L V R Y F L D K T L T S R L G I   DAPK-6
131  D H K D V V T L L A E G L R E S R K H I E D E K L V R Y F L D K T L T S R L G I   g924921

201  R M L A T H H L A L H E D K P D F V G I I C T R L S P K K I I E K W V D F A R R   DAPK-6
171  R M L A T H H L A L H E D K P D F V G I I C T R L S P K K I I E K W V D F A R R   g924921
```

FIGURE 6A

```
241  L C E H K Y G N A P R V R I N G H V A A A R F P F I P M P L D Y I L P E L L K N A   DAPK-6
211  L C E H K Y G N A P R V R I N G H V A A A R F P F I P M P L D Y I L P E L L K N A   g924921

281  M R A T M E S H L D T P Y N V P D V V I T I A N N D V D L I I R I S D R G G G I     DAPK-6
251  M R A T M E S H L D T P Y N V P D V V I T I A N N D V D L I I R I S D R G G G I     g924921

321  A H K D L D R V M D Y H F T T A E A S T Q D P R I S P L F G H L D M H S G A Q S     DAPK-6
291  A H K D L D R V M D Y H F T T A E A S T Q D P R I S P L F G H L D M H S G G Q S     g924921

361  G P M H G F G F G L P T S R A Y A E Y L G G S L Q L Q S L Q G I G T D V Y L R L     DAPK-6
331  G P M H G F G F G L P T S R A Y A E Y L G G S L Q L Q S L Q G I G T D V Y L R L     g924921

401  R H I D G R E E S F R I                                                             DAPK-6
371  R H I D G R E E S F R I                                                             g924921
```

FIGURE 6B

```
  1 MLEKLEFEDEAVEDSE------SGVYMRFMRSHKCYD    DAPK-7
  1 METVISSDSSPAVENEHPQETPESNNSVYTSFMKSHRCYD g1335856

32 IVPTSSKLVVFDTTLQVKKAFFALVANGVRAAPLWESKKQ  DAPK-7
 41 LIPTSSKLVVFDTSLQVKKAFFALVTNGVRAAPLWDSKKQ  g1335856

72 SFVGMLTITDFINILHRYYKSPMVQIYELEEHKIETWREL  DAPK-7
 81 SFVGMLTITDFINILHRYYKSALVQIYELEEHKIETWREV  g1335856

112 YLQETFKPLVNISPDASLFDAVYSLIKNKIHRLPVIDPIS  DAPK-7
121 YLQDSFKPLVCISPNASLFDAVSSLIRNKIHRLPVIDPES  g1335856

152 GNALYILTHKRILKFLQLFMSDMPKPAFMKQNLDELGIGT  DAPK-7
161 GNTLYILTHKRILKFLKLFITEFPKPEFMSKSLEELQIGT  g1335856
```

FIGURE 7A

```
192 YHNIAFIHPDTPIIKALNIFVERRISALPVVDESGKVVDI   DAPK-7
201 YANIAMVRTTPVYVALGIFVQHRVSALPVVDEKGRVVDI    g1335856

232 YSKFDVINLAAEKTYNNLDITVTQALQHRSQYFEGVVKCN   DAPK-7
241 YSKFDVINLAAEKTYNNLDVSVTKALQHRSHYFEGVLKCY   g1335856

272 KLEILETIVDRIVRAEVHRLVVVNEADSIVGIISLSDILQ   DAPK-7
281 LHETLETIINRLVEAEVHRLVVVDENDVVKGIVSLSDILQ   g1335856

312 ALILTPAGAKQKETETE                         DAPK-7
321 ALVLTGGEKKP                               g1335856
```

FIGURE 7B

DISEASE ASSOCIATED PROTEIN KINASES

This application is a divisional application of U.S. application Ser. No. 08/878,989, filed Jun. 19, 1997, now U.S. Pat. No. 5,885,803.

FIELD OF THE INVENTION

This invention relates to nucleic acid and amino acid sequences of human protein kinases which are important in disease and to the use of these sequences in the diagnosis, prevention, and treatment of diseases associated with cell proliferation.

BACKGROUND OF THE INVENTION

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contain specific residues and motifs or patterns of amino acids that are characteristic of that subdomain and are highly conserved (Hardie, G. and Hanks, S. (1995) *The Protein Kinase Facts Books,* Vol 1:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADP ribose, arachidonic acid, diacylglycerol and calcium-calmodulin. The cyclic-AMP dependent protein kinases (PKA) are important members of the STK family. Cyclic-AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine,* McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) EMBO Journal 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) J. Biol Chem. 15:8675–81). Mammaliam AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781–783). MAP kinase signaling pathways are present in mammalian cells as well as in yeast. The extracellular stimuli which activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) J. Biol. Chem. 271:19402–8). PRK is related to the polo (derived from Drosophila polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs which then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H. and Tonks N. K. (1992) Annu Rev Cell Biol 8:463–93). Regulation of PTK activity may therefore be an important strategy in controlling some types of cancer.

An additional family of protein kinases previously thought to exist only in procaryotes is the histidine protein kinase family (HPK). HPKs bear little homology with mammalian STKs or PTKs but have distinctive sequence motifs of their own (Davie, J. R. et al. (1995) J. Biol. Chem. 270:19861–67). A histidine residue in the N-terminal half of the molecule (region I) is an autophosphorylation site. Three additional motifs located in the C-terminal half of the molecule include an invariant asparagine residue in region II and two glycine-rich loops characteristic of nucleotide binding domains in regions III and IV. Recently a branched chain alpha-ketoacid dehydrogenase kinase has been found with characteristics of HPK in rat (Davie et al., supra).

The discovery of new human disease associated protein kinases which are important in disease development, and the polynucleotides encoding them, satisfies a need in the art by providing new compositions which are useful in the diagnosis, prevention and treatment of diseases associated with cell proliferation, particularly and immune responses and cancers.

SUMMARY OF THE INVENTION

The invention features substantially purified polypeptides, human disease associated protein kinases, collectively referred to as DAPK and individually referred to as DAPK-1, DAPK-2, DAPK-3, DAPK4, DAPK-5, DAPK-6, and DAPK-7, having the amino acid sequences selected from the group consisting of SEQ ID NO: 1, SEQ ID NO:2, SEQ ID NO:3, SEQ ID NO:4, SEQ ID NO:5, SEQ ID NO:6, and SEQ ID NO:7, respectively.

The invention further provides isolated and substantially purified polynucleotide sequences encoding DAPK. In a particular aspect, the polynucleotide is at least one of the nucleotide sequences selected from the group consisting of SEQ ID NO:8, SEQ ID NO:9, SEQ ID NO: 10, SEQ ID NO: 11, SEQ ID NO:12, SEQ ID NO: 13, and SEQ ID NO: 14.

In addition, the invention provides a polynucleotide sequence, or fragment thereof, which hybridizes under stringent conditions to any of the polynucleotide sequences of SEQ ID NOs:8–14. In another aspect the invention provides compositions comprising isolated and purified polynucleotide sequences of SEQ ID NOs:8–14 or fragments thereof.

The invention further provides a polynucleotide sequence comprising the complement or fragments thereof of any one of the polynucleotide sequences encoding DAPK. In another aspect the invention provides compositions comprising isolated and purified polynucleotide sequences comprising the complements of SEQ ID NOs:8–14, or fragments thereof.

The present invention further provides an expression vector containing at least a fragment of any one of the polynucleotide sequences of SEQ ID NOs:8–14. In yet another aspect, the expression vector containing the polynucleotide sequence is contained within a host cell.

The invention also provides a method for producing a polypeptide or a fragment thereof, the method comprising the steps of: a) culturing the host cell containing an expression vector containing at least a fragment of the polynucleotide sequence encoding an DAPK under conditions suitable for the expression of the polypeptide; and b) recovering the polypeptide from the host cell culture.

The invention also provides a pharmaceutical composition comprising a substantially purified DAPK in conjunction with a suitable pharmaceutical carrier.

The invention also provides a purified antagonist of DAPK. In one aspect the invention provides a purified antibody which binds to an DAPK.

Still further, the invention provides a purified agonist of DAPK.

The invention also provides a method for treating or preventing a cancer comprising administering to a subject in need of such treatment an effective amount of a pharmaceutical composition containing DAPK.

The invention also provides a method for treating or preventing a cancer comprising administering to a subject in need of such treatment an effective amount of a pharmaceutical composition containing DAPK The invention also provides a method for treating or preventing an immune response associated with the increased expression or activity of DAPK comprising administering to a subject in need of such treatment an effective amount of an antagonist of DAPK.

The invention also provides a method for stimulating cell proliferation comprising administering to a cell an effective amount of DAPK.

The invention also provides a method for detecting a polynucleotide which encodes a disease associated protein kinase in a biological sample comprising the steps of: a) hybridizing a polynucleotide sequence complementary to a polynucleotide encoding DAPK to nucleic acid material of a biological sample, thereby forming a hybridization complex; and b) detecting the hybridization complex, wherein the presence of the complex correlates with the presence of a polynucleotide encoding the disease associated protein kinase in the biological sample.

The invention also provides a microarray which contains at least a fragment of at least one of the polynucleotide sequences encoding DAPK. In a particular aspect, the microarray contains at least a fragment of at least one of the sequences selected from the group consisting of SEQ ID NO:8, SEQ ID NO:9, SEQ ID NO:10, SEQ ID NO: 11, SEQ ID NO:12, SEQ ID NO:13, and SEQ ID NO:14.

The invention also provides a method for the simultaneous detection of the levels of expression of polynucleotides which encode disease associated protein kinases in a biological sample comprising the steps of: a) hybridizing said microarray to labeled complementary nucleotides of a biological sample, comprising at least a fragment of at least one of the polynucleotides encoding DAPK, thereby forming hybridization complexes; and b) quantifying expression, wherein the signal produced by the hybridization complexes correlates with expression of particular polynucleotides encoding disease associated protein kinases in the biological sample. In a preferred embodiment, prior to hybridization, the nucleic acid material of the biological sample is amplified and labeled by the polymerase chain reaction.

BRIEF DESCRIPTION OF THE FIGURES

FIGS. 1A, 1B, and 1C show the amino acid sequence alignments between DAPK-1 (SEQ ID NO:1) and the human proliferation-related protein kinase, PRK (GI 1488263; SEQ ID NO: 15), produced using the multisequence alignment program of DNASTAR software (DNASTAR Inc, Madison Wis.).

FIGS. 2A, and 2B show the amino acid sequence alignments between DAPK-2 (SEQ ID NO:3) and the human vaccinia virus-related protein kinase, VRK1 (GI 1827450; SEQ ID NO: 16), produced using the multisequence alignment program of DNASTAR software.

FIGS. 3A and 3B show the amino acid sequence alignments between DAPK-3 (SEQ ID NO:3) and the rat MAP-kinase, MEK2 (GI 303804; SEQ ID NO: 17), produced using the multisequence alignment program of DNASTAR software.

FIGS. 4A and 4B show the amino acid sequence alignments between DAPK-4 (SEQ ID NO:4) and the human nuclear protein kinase, Ndr (GI 854170; SEQ ID NO: 18), produced using the multisequence alignment program of DNASTAR software.

FIGS. 5A and 5B show the amino acid sequence alignments between DAPK-5 (SEQ ID NO:5) and the human CaM kinase, CaMKI (GI 790790; SEQ ID NO. 19), produced using the multisequence alignment program of DNASTAR software.

FIGS. 6A and 6B show the amino acid sequence alignments between DAPK-6 (SEQ ID NO:6) and the rat branched-chain alpha ketoacid dehydrogenase kinase, BCKDH kinase (GI 924921; SEQ ID NO:20), produced using the multisequence alignment program of DNASTAR software.

FIGS. 7A and 7B show the amino acid sequence alignments between DAPK-7 (SEQ ID NO:7) and the human 5'-AMP activated protein kinase gamma subunit, AMPK-gamma (GI 1335856; SEQ ID NO:21), produced using the multisequence alignment program of DNASTAR software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, arrays and methodologies which are reported in the publications which might be used in connection with the invention. Nothing herein is to be construed as an admission that the invention is not entitled to antedate such disclosure by virtue of prior invention.

DEFINITIONS

DAPK, as used herein, refers to the amino acid sequences of substantially purified DAPK obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to DAPK, increases or prolongs the duration of the effect of DAPK. Agonists may include proteins, nucleic acids, carbohydrates, or any other molecules which bind to and modulate the effect of DAPK.

An "allele" or "allelic sequence", as used herein, is an alternative form of the gene encoding DAPK. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding DAPK as used herein include those with deletions, insertions, or substitutions of different nucleotides resulting in a polynucleotide that encodes the same or a functionally equivalent DAPK. Included within this definition are polymorphisms which may or may not be readily detectable using a particular oligonucleotide probe of the polynucleotide encoding DAPK, and improper or unexpected hybridization to alleles, with a locus other than the normal chromosomal locus for the polynucleotide sequence encoding DAPK. The encoded protein may also be "altered" and contain deletions, insertions, or substitutions of amino acid residues which produce a silent change and result in a functionally equivalent DAPK. Deliberate amino acid substitutions may be made on the basis of similarity in polarity, charge, solubility, hydrophobicity, hydrophilicity, and/or the amphipathic nature of the residues as long as the biological or immunological activity of DAPK is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of DAPK are preferably about 5 to about 15 amino acids in length and retain the biological activity or the immunological activity of DAPK. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "antagonist" as used herein, refers to a molecule which, when bound to DAPK, decreases the amount or the duration of the effect of the biological or immunological activity of DAPK. Antagonists may include proteins, nucleic acids, carbohydrates, or any other molecules which decrease the effect of DAPK.

As used herein, the term "antibody" refers to intact molecules as well as fragments thereof, such as Fab, F(ab')$_2$, and Fv, which are capable of binding the epitopic determinant. Antibodies that bind DAPK polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic DAPK, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding DAPK (SEQ ID NOs:8–14) or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.). "Consensus", as used herein, refers to a nucleic acid sequence which has been resequenced to resolve uncalled bases, has been extended using XL-PCR Kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence .

The term "correlates with expression of a polynucleotide", as used herein, indicates that the detection of the presence of a ribonucleic acid that is similar to a polynucleotide encoding an DAPK by northern analysis is indicative of the presence of mRNA encoding DAPK in a sample and thereby correlates with expression of the transcript from the polynucleotide encoding the protein.

The term "DAPK" refers to any one or all of the human polypeptides, DAPK-1, DAPK-2, DAPK-3, DAPK4, DAPK-5, DAPK6, DAPK-7, and DAPK-8.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to DAPK or the encoded DAPK. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10 K to 10 M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule. "Microarray" refers to an array (or arrangement) of distinct oligonucleotides synthesized on a substrate, such as paper, nylon or other type of membrane, filter, gel, polymer, chip, glass slide, or any other suitable support.

The term "modulate", as used herein, refers to a change in the activity of DAPK. For example, modulation may cause an increase or a decrease in protein activity, binding characteristics, or any other biological, functional or immunological properties of DAPK.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of an DAPK encompasses the full-length DAPK and fragments thereof.

The term "sample", as used herein, is used in its broadest sense. A biological sample suspected of containing nucleic acid encoding DAPK, or fragments thereof, or DAPK itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5°. below the melting temperature of the probe to about 20°. to 25°. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively. "Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of DAPK, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of human disease associated protein kinases (DAPK) and the polynucleotides encoding DAPK, and the use of these compositions for the diagnosis, prevention, or treatment of diseases associated with cell proliferation. Table I shows the protein and nucleotide sequence identification numbers, Incyte Clone number, cDNA library, NCBI homolog and NCBI sequence identifier for each of the human disease associated protein kinases disclosed herein.

TABLE 1

| Polypeptide | Polynucleotide | Inctye Clone | Incyte Library | NCBI Homolog |
|---|---|---|---|---|
| Seq 1 | Seq 8 | 39043 | HUVENOB01 | Human GI 1488263 |
| Seq 2 | Seq 9 | 40194 | TBLYNOT01 | Human GI 1827450 |
| Seq 3 | Seq 10 | 402339 | TMLR3DT01 | Rat GI 303804 |
| Seq 4 | Seq 11 | 705365 | SYNORAT04 | Human GI 854170 |
| Seq 5 | Seq 12 | 827431 | PROSNOT06 | Human GI 790790 |
| Seq 6 | Seq 13 | 1340712 | COLNTUT03 | Rat GI 924921 |
| Seq 7 | Seq 14 | 1452972 | PENITUT01 | Human GI 1335856 |

DAPK-I (SEQ ID NO:1) was first identified in Incyte Clone 39043 from the HUVENOB01 cDNA library using a computer search for amino acid sequence alignments. A consensus sequence, SEQ ID NO:8, was derived from the extended and overlapping nucleic acid sequences: Incyte Clones 39043/ HUVENOB01, 86618/ LIVRNOT01, 241996/ HIPONOT01, 486079/ HNT2RAT01, 1255087/ LUNGFET03, 1294238/ PGANNOT03, and 2375745/ ISLTNOT01.

Therefore, in one embodiment, the invention encompasses a polypeptide comprising the amino acid sequence of SEQ ID NO:1. DAPK-1 is 685 amino acids in length and has a potential ATP-binding sequence at $G_{89}KGGFAKC$. As shown in FIG. 1, DAPK-1 has sequence homology with cytokine-inducible, human proliferation-related kinase, PRK (GI 1488263). In particular, DAPK-1 and PRK share 53 % homology. DAPK-1 and PRK share the ATP binding region described above and, in addition, share a presumed regulatory sequence at $K_{506}WVDYS$ common to members of the polo family of protein kinases. DAPK-I is associated with cDNA libraries which are immortalized or cancerous and show inflammatory or immune responses.

DAPK-2 (SEQ ID NO:2) was first identified in Incyte Clone 40194 from the TBLYNOT01 cDNA library using a computer search for amino acid sequence alignments. A consensus sequence, SEQ ID NO:9, was derived from the extended and overlapping nucleic acid sequences: Incyte Clones 40194/ TBLYNOT01, 278198/ TESTNOT03, and 1683885/PROSNOT15.

Therefore, in one embodiment, the invention encompasses a polypeptide comprising the amino acid sequence of SEQ ID NO:2. DAPK-2 is 448 amino acids in length and has a potential ATP-binding sequence at $G_{36}SGGFGLI$ and an STK specific signature sequence at $Y_{62}VHGDVKAANLLL$. As shown in FIG. 2, DAPK-2 has sequence homology with the human vaccina virus related kinase, VRK1 (GI 1827450). In particular, DAPK-2 and VRK1 share 65% homology. DAPK-2 and VRK1 share the glycine-rich ATP-binding sequence and the STK signature sequence described above. DAPK-2 is associated with cDNA libraries which are immortalized or cancerous and show inflammatory or immune responses.

DAPK-3 (SEQ ID NO:3) was first identified in Incyte Clone 402339 from the TMLR3DT01cDNA library using a computer search for amino acid sequence alignments. A consensus sequence, SEQ ID NO:10, was derived from the extended and overlapping nucleic acid sequences: Incyte Clones 402339/ TMLR3DT01, 495759/ HNT2NOT01, and 1931950/COLNNOT16.

Therefore, in one embodiment, the invention encompasses a polypeptide comprising the amino acid sequence of SEQ ID NO:3. DAPK-3 is 400 amino acids in length and contains various sequence motifs characteristic of the catalytic domain of protein kinases. An ATP-binding sequence is found at $G_{79}$AGNGGVV of subdomain I, and $K_{101}$ and $E_{118}$ are invariant residues found in subdomains II and II, respectively. The "catalytic loop" of subdomain VIB is found in the sequence $H_{112}$RDVKPSN, and the triplet codons $D_{212}$FG and $A_{275}$PE are characteristic of subdomains VII and VIII, respectively. As shown in FIG. 3, DAPK-3 has sequence homology with the rat MAP kinase kinase, MEK2 (GI 303804). In particular, DAPK-3 and MEK3 share 94% homology. DAPK-3 is associated with cDNA libraries which are immortalized or cancerous and show inflammatory or immune responses.

DAPK-4 (SEQ ID NO:4) was first identified in Incyte Clone 705365 from the SYNORAT04 cDNA library using a computer search for amino acid sequence alignments. A consensus sequence, SEQ ID NO: 11, was derived from the extended and overlapping nucleic acid sequences: Incyte Clones 705365/ SYNORAT04, 2529903/ GBLANOT02, and 2729238/ OVARTUT05.

Therefore, in one embodiment, the invention encompasses a polypeptide comprising the amino acid sequence of SEQ ID NO:4. DAPK-4 is 464 amino acids in length and contains various sequence motifs characteristic the catalytic domain of protein kinases. An ATP-binding sequence is found at $G_{79}$RGAFGEV and the catalytic loop is found at $H_{211}$RDIKPDN. DAPK-4 also contains a nuclear localization signal at $K_{266}$RKAETWKKNR. As shown in FIG. 4, DAPK-4 has sequence homology with human nuclear protein kinase, Ndr (GI 854170). In particular, DAPK-4 and Ndr share 87% homology. DAPK-4 is associated with cDNA libraries which are immortalized or cancerous and show inflammatory or immune responses.

DAPK-5 (SEQ ID NO:5) was first identified in Incyte Clone 827431 from the PROSNOT06 cDNA library using a computer search for amino acid sequence alignments. A consensus sequence, SEQ ID NO: 12, was derived from the extended and overlapping nucleic acid sequences: Incyte Clones 755081, 758002 and 760552/ BRAITUT02, 827431/ PROSNOT06, 1286067/ COLNNOT16, and 1503272/ BRAITUT07.

Therefore, in one embodiment, the invention encompasses a polypeptide comprising the amino acid sequence of SEQ ID NO:5. DAPK-5 is 343 amino acids in length and contains various sequence motifs characteristic of the catalytic domain of protein kinases. An ATP-binding sequence is found at $G_{22}$SGAFSEV and the catalytic loop is found at $H_{134}$RDLKPEN. The triplet codons $D_{157}$FG and $A_{180}$PE characteristic of subdomains VII and VIII, respectively, are also found. As shown in FIG. 5, DAPK-5 has sequence homology with the human CaM-kinase, CaMKI (GI 790790). In particular, DAPK-5 and CAMKI share 64% homology. In addition to the typical protein kinase motifs mentioned above, DAPK-5 and CaMKI share $T_{171}$ which is a phosphorylation site for CaMKI kinase and an autoinhibitory and CaM-binding domain found between L280 and $L_{313}$ of DAPK-5. DAPK-5 is associated with cDNA libraries which are immortalized or cancerous.

DAPK-6 (SEQ ID NO:6) was first identified in Incyte Clone 1340712 from the COLNTUT03 cDNA library using a computer search for amino acid sequence alignments. A consensus sequence, SEQ ID NO: 13, was derived from the extended and overlapping nucleic acid sequences: Incyte Clones 1340712/ COLNTUT03, 1350483/ LATRTUT02 and 2631495/ COLNTUTI 5.

Therefore, in one embodiment, the invention encompasses a polypeptide comprising the amino acid sequence of SEQ ID NO:6. DAPK-6 is 412 amino acids in length and has characteristics of a histidine protein kinase (HPK). $H_{211}$ in DAPK-6 corresponds to a potential autophosphorylation site in subdomain I of HPK, and $N_{279}$ is also an invariant residue of subdomain II. The sequences $D_{315}$RGGG and $G_{365}$FGFG are characteristic of subdomain III and IV of HPK. As shown in FIG. 6, DAPK-6 has sequence homology with a rat branched-chain alpha-ketoacid dehydrogenase kinase, BCKDH kinase (GI 924921). In particular, DAPK-6 and BCKDH kinase share 98% homology. BCKDH kinase shares the characteristic sequences of HPKs described above, but differs by the presence of a distinctive N-terminal leader sequence in DAPK-6 that may target DAPK-6 to a different subcellular site. DAPK-6 is associated with cDNA libraries which are immortalized or cancerous and show inflammatory or immune responses.

DAPK-7 (SEQ ID NO:7) was first identified in Incyte Clone 1452972 from the PENITUT01 cDNA library using a computer search for amino acid sequence alignments. A consensus sequence, SEQ ID NO: 14, was derived from the extended and overlapping nucleic acid sequences: Incyte Clones 307571/ HEARNOT01, 842220/ PROSTUT05, 1364737/SCORNON02, 1452972 and 1454802/ PENITUT01, and 1479332/ CORPNOT02.

Therefore, in one embodiment, the invention encompasses a polypeptide comprising the amino acid sequence of SEQ ID NO:7. DAPK-7 is 328 amino acids in length and has potential cAMP-dependent protein kinase phosphorylation sites at $S_{72}$ and S217. As shown in FIG. 7, DAPK-7 has sequence homology with human fetal liver AMPK gamma-subunit (GI 1335856). In particular, DAPK-7 and AMPK gamma share 73% homology. Several sequences that are conserved among AMPK gamma isoforms are shared by DAPK-7 and AMPK gamma. These include $L_{77}$TITDFINLHRYYKS, $S_{217}$ALPVVDE, $V_{228}$VDIYSKFDVI, and $A_{286}$EVHRRLVVV. Sequence differences between DAPK-7 and other AMPK gamma isoforms, particularly the distinctive N-terminal portion of DAPK-7, $L_2$EKLEFEDEAVEDSESG, may signify different tissue expression and/or regulatory roles for DAPK-7. DAPK-7 is associated with cDNA libraries which are immortalized or cancerous and show inflammatory or immune responses.

The invention also encompasses DAPK variants which retain the biological or functional activity of DAPK. A preferred DAPK variant is one having at least 80%, and more preferably 90%, amino acid sequence identity to the DAPK amino acid sequence. A most preferred DAPK variant is one having at least 95% amino acid sequence identity to an DAPK disclosed herein (SEQ ID NOs: 1–7).

The invention also encompasses polynucleotides which encode DAPK. Accordingly, any nucleic acid sequence which encodes the amino acid sequence of DAPK can be used to produce recombinant molecules which express DAPK. In a particular embodiment, the invention encompasses a polynucleotide consisting of a nucleic acid sequence selected from the group consisting of SEQ ID NOs:8–14.

It will be appreciated by those skilled in the art that as a result of the degeneracy of the genetic code, a multitude of nucleotide sequences encoding DAPK, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring DAPK, and all such variations are to be considered as being specifically disclosed.

Although nucleotide sequences which encode DAPK and its variants are preferably capable of hybridizing to the nucleotide sequence of the naturally occurring DAPK under appropriately selected conditions of stringency, it may be advantageous to produce nucleotide sequences encoding DAPK or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding DAPK and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode DAPK and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding DAPK or any fragment thereof.

Also encompassed by the invention are polynucleotide sequences that are capable of hybridizing to the claimed nucleotide sequences, and in particular, those shown in SEQ ID NOs:8–14, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE DNA polymerase (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by (GIBCO/BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI CATALYST and 373 and 377 DNA SEQUENCERS (Perkin Elmer).

The nucleic acid sequences encoding DAPK may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA S polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is usefull in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR Software, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode DAPK may be used in recombinant DNA molecules to direct expression of DAPK, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express DAPK.

As will be understood by those of skill in the art, it may be advantageous to produce DAPK-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter DAPK encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding DAPK may be ligated to a heterologous sequence to encode a fusion protein. For example, to screen peptide libraries for inhibitors of DAPK activity, it may be useful to encode a chimeric DAPK protein that can be recognized by a commercially available antibody. A fusion protein may also be engineered to contain a cleavage site located between the DAPK encoding sequence and the heterologous protein sequence, so that DAPK may be cleaved and purified away from the heterologous moiety.

In another embodiment, sequences encoding DAPK may be synthesized, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser. 7:225–232). Alternatively, the protein itself may be produced using chemical methods to synthesize the amino acid sequence of DAPK, or a fragment thereof For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of DAPK, or any part thereof, may be altered during direct synthesis and/or combined using chemical methods with sequences from other proteins, or any part thereof, to produce a variant polypeptide.

In order to express a biologically active DAPK, the nucleotide sequences encoding DAPK or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding DAPK and appropriate transcriptional and translational control elements. These methods include in vitro recombinant DNA techniques, synthetic techniques, and in vivo genetic recombination. Such techniques are described in Sambrook, J. et al. (1989) *Molecular Cloning, Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding DAPK. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding DAPK, vectors based on SV40 or EBV may be used with an appropriate selectable marker.

In bacterial systems, a number of expression vectors may be selected depending upon the use intended for DAPK. For example, when large quantities of DAPK are needed for the induction of antibodies, vectors which direct high level expression of fusion proteins that are readily purified may be used. Such vectors include, but are not limited to, the multifunctional *E. coli* cloning and expression vectors such as BLUESCRIPT phagemid (Stratagene), in which the sequence encoding DAPK may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding DAPK may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express DAPK. For example, in one such system, *Autographa californica* nuclear polyhedrosis virus (AcNPV) is used as a vector to express foreign genes in *Spodoptera frugiperda* cells or in Trichoplusia larvae. The sequences encoding DAPK may be cloned into a non-essential region of the virus, such as the polyhedrin gene, and placed under control of the polyhedrin promoter. Successful insertion of DAPK will render the polyhedrin gene inactive and produce recombinant virus lacking coat protein. The recombinant viruses may then be used to infect, for example, *S. frugiperda* cells or Trichoplusia larvae in which DAPK may be expressed (Engelhard, E. K. et al. (1994) Proc. Nat. Acad. Sci. 91 :3224–3227).

In mammalian host cells, a number of viral-based expression systems may be utilized. In cases where an adenovirus is used as an expression vector, sequences encoding DAPK may be ligated into an adenovirus transcription/translation complex consisting of the late promoter and tripartite leader sequence. Insertion in a non-essential E1 or E3 region of the viral genome may be used to obtain a viable virus which is capable of expressing DAPK in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to I OM are constructed and delivered via conventional delivery methods (liposomes, polycationic amino polymers, or vesicles) for therapeutic purposes.

Specific initiation signals may also be used to achieve more efficient translation of sequences encoding DAPK. Such signals include the ATG initiation codon and adjacent sequences. In cases where sequences encoding DAPK, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express DAPK may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–5 1). Recently, the use of visible markers has gained popularity with such markers as anthocyanins, B glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding DAPK is inserted within a marker gene sequence, transformed cells containing sequences encoding DAPK can be identified by the absence of marker gene function. Alternatively, a marker gene can be placed in tandem with a sequence encoding DAPK under the control of a single promoter. Expression of the marker gene in response to induction or selection usually indicates expression of the tandem gene as well.

Alternatively, host cells which contain the nucleic acid sequence encoding DAPK and express DAPK may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein. The presence of polynucleotide sequences encoding DAPK can be detected by DNA-DNA or DNA-RNA hybridization or amplification using probes or fragments or fragments of polynucleotides encoding DAPK. Nucleic acid amplification based assays involve the use of oligonucleotides or oligomers based on the sequences encoding DAPK to detect transformants containing DNA or RNA encoding DAPK.

A variety of protocols for detecting and measuring the expression of DAPK, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on DAPK is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding DAPK include oligolabeling, nick translation, end-labeling or PCR amplification using a labeled nucleotide. Alternatively, the sequences encoding DAPK, or any fragments thereof may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Miss.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding DAPK may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode DAPK may be designed to contain signal sequences which direct secretion of DAPK through a prokaryotic or eukaryotic cell membrane. Other constructions may be used to join sequences encoding DAPK to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences such as those specific for Factor XA or enterokinase (Invitrogen, San Diego, Calif.) between the purification domain and DAPK may be used to facilitate purification. One such expression vector provides for expression of a fusion protein containing DAPK and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying DAPK from the fusion protein. A discussion of vectors which contain fusion proteins is provided in Kroll, D. J. et al. (1993; DNA Cell Biol. 12:441–453).

In addition to recombinant production, fragments of DAPK may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesizer (Perkin Elmer). Various fragments of DAPK may be chemically synthesized separately and combined using chemical methods to produce the full length molecule.

THERAPEUTICS

Chemical and structural homology exits among the human protein kinases of the invention. The expression of DAPK is closely associated with cell proliferation. Therefore, in cancers or immune disorders where DAPK is being expressed, or is promoting cell proliferation; it is desirable to decrease the expression of DAPK. In cancers where expression of DAPK is decreased, it is desirable to provide the protein or increase the expression of DAPK.

In one embodiment, DAPK or a fragment or derivative thereof may be administered to a subject to prevent or treat cancer which is associated with decreased expression of DAPK. Such cancers include, but are not limited to, adenocarcinoma, leukemia, lymphoma, melanoma, myeloma, sarcoma, and teratocarcinoma and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, an agonist which is specific for DAPK may be administered to a subject to prevent or treat cancer including, but not limited to, those cancers listed above. In another further embodiment, a vector capable of expressing DAPK, or a fragment or a derivative thereof, may be administered to a subject to prevent or treat cancer including, but not limited to, those cancers listed above.

In a further embodiment, antagonists which decrease the expression and activity of DAPK may be administered to a subject to prevent or treat cancer which is associated with increased expression of DAPK. Such cancers include, but are not limited to, adenocarcinoma, leukemia, lymphoma, melanoma, myeloma, sarcoma, and teratocarcinoma and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind DAPK may be used directly as an antagonist or indirectly as a targeting or delivery mechanism for bringing a pharmaceutical agent to cells or tissue which express DAPK.

In another embodiment, a vector expressing the complement of the polynucleotide encoding DAPK may be administered to a subject to treat or prevent cancer including, but not limited to, those cancers listed above.

In one embodiment, an antagonist of DAPK may be administered to a subject to prevent or treat an immune response. Such responses may be associated with AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, antibodies which specifically bind DAPK may be used directly as an antagonist or indirectly as a targeting or delivery mechanism for bringing a pharmaceutical agent to cells or tissue which express DAPK.

In another embodiment, a vector expressing the complement of the polynucleotide encoding DAPK may be administered to a subject to treat or prevent an immune response including, but not limited to, those listed above.

In a further embodiment, DAPK or a fragment or derivative thereof may be added to cells to stimulate cell proliferation. In particular, DAPK may be added to a cell in culture or cells in vivo using delivery mechanisms such as liposomes, viral based vectors, or electroinjection for the purpose of promoting cell proliferation and tissue or organ regeneration. Specifically, DAPK may be added to a cell, cell line, tissue or organ culture in vitro or ex vivo to stimulate cell proliferation for use in heterologous or autologous transplantation. In some cases, the cell will have been preselected for its ability to fight an infection or a cancer or to correct a genetic defect in a disease such as sickle cell anemia, thalassemia, cystic fibrosis, or Huntington's chorea.

In another embodiment, an agonist which is specific for DAPK may be administered to a cell to stimulate cell proliferation, as described above.

In another embodiment, a vector capable of expressing DAPK, or a fragment or a derivative thereof, may be administered to a cell to stimulate cell proliferation, as described above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of DAPK may be produced using methods which are generally known in the art. In particular, purified DAPK may be used to produce antibodies or to screen libraries of pharmaceutical agents to identify those which specifically bind DAPK.

Antibodies to DAPK may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with DAPK or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to DAPK have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of DAPK amino acids may be fused with those of another protein such as keyhole limpet hemocyanin and antibody produced against the chimeric molecule.

Monoclonal antibodies to DAPK may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce DAPK-specific single chain antibodies. Antibodies with related specificity, but of distinct idiotypic composition, may be generated by chain shuffling from random combinatorial immunoglubulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299). Antibody fragments which contain specific binding sites for DAPK may also be generated. For example, such fragments include, but are not limited to, the F(ab')2 fragments which can be produced by pepsin digestion of the antibody molecule and the Fab fragments which can be generated by reducing the disulfide bridges of the F(ab'2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between DAPK and its specific antibody. A two-site, monoclonal-based immunoassay utilizing monoclonal antibodies reactive to two non-interfering DAPK epitopes is preferred, but a competitive binding assay may also be employed (Maddox, supra).

In another embodiment of the invention, the polynucleotides encoding DAPK, or any fragment or complement thereof, may be used for therapeutic purposes. In one aspect, the complement of the polynucleotide encoding DAPK may be used in situations in which it would be desirable to block the transcription of the MRNA. In particular, cells may be transformed with sequences complementary to polynucleotides encoding DAPK. Thus, complementary molecules or fragments may be used to modulate DAPK activity, or to achieve regulation of gene function. Such technology is now well known in the art, and sense or antisense oligonucleotides or larger fragments, can be designed from various locations along the coding or control regions of sequences encoding DAPK.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding DAPK. These techniques are described both in Sambrook et al. (supra) and in Ausubel et al. (supra).

Genes encoding DAPK can be turned off by transforming a cell or tissue with expression vectors which express high levels of a polynucleotide or fragment thereof which encodes DAPK. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding DAPK (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding DAPK.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding DAPK. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of DAPK, antibodies to DAPK, mimetics, agonists, antagonists, or inhibitors of DAPK. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art. The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of DAPK, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example DAPK or fragments thereof, antibodies of DAPK, agonists, antagonists or inhibitors of DAPK, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind DAPK may be used for the diagnosis of conditions or diseases characterized by expression of DAPK, or in assays to monitor patients being treated with DAPK, agonists, antagonists or inhibitors. The antibodies useful for diagnostic purposes may be prepared in the same manner as those described above for therapeutics. Diagnostic assays for DAPK include methods which utilize the antibody and a label to detect DAPK in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring DAPK are known in the art and provide a basis for diagnosing altered or abnormal levels of DAPK expression. Normal or standard values for DAPK expression are established by combining body fluids or cell extracts taken from normal mammalian subjects, preferably human, with antibody to DAPK under conditions suitable for complex formation The amount of standard complex formation may be quantified by various methods, but preferably by photometric, means. Quantities of DAPK expressed in control and disease, samples from biopsied tissues are compared with the standard values. Deviation between standard and subject values establishes the parameters for diagnosing disease.

In another embodiment of the invention, the polynucleotides encoding DAPK may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of DAPK may be correlated with disease. The diagnostic assay may be used to distinguish between absence, presence, and excess expression of DAPK, and to monitor regulation of DAPK levels during therapeutic intervention.

In one aspect, hybridization with PCR probes which are capable of detecting polynucleotide sequences, including genomic sequences, encoding DAPK or closely related molecules, may be used to identify nucleic acid sequences which encode DAPK. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding DAPK, alleles, or related sequences.

Probes may also be used for the detection of related sequences, and should preferably contain at least 50% of the nucleotides from any of the DAPK encoding sequences. The hybridization probes of the subject invention may be DNA or RNA and derived from the nucleotide sequence of SEQ ID NO:8–14 or from genomic sequence including promoter, enhancer elements, and introns of the naturally occurring DAPK.

Means for producing specific hybridization probes for DNAs encoding DAPK include the cloning of nucleic acid sequences encoding DAPK or DAPK derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidinibiotin coupling systems, and the like.

Polynucleotide sequences encoding DAPK may be used for the diagnosis of conditions, disorders, or diseases which are associated with either increased or decreased expression of DAPK. Examples of such conditions or diseases include adenocarcinoma, leukemia, lymphoma, melanoma, myeloma, sarcoma, teratocarcinoma, and cancers of the adrenal gland, bladder, bone, brain, breast, cervix, gall bladder, ganglia, gastrointestinal tract, heart, kidney, liver, lung, bone marrow, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and thyroiditis. The polynucleotide sequences encoding DAPK may be used in Southern or northern analysis, dot blot, or other membrane-based technologies; in PCR technologies; or in dipstick, pin, ELISA assays or microarrays utilizing fluids or tissues from patient biopsies to detect altered DAPK expression. Such qualitative or quantitative methods are well known in the art.

In a particular aspect, the nucleotide sequences encoding DAPK may be useful in assays that detect activation or induction of various cancers, particularly those mentioned above. The nucleotide sequences encoding DAPK may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding DAPK in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of DAPK, a normal or standard profile for expression is established. This may be accomplished by combining body fluids or cell extracts taken from normal subjects, either animal or human, with a sequence, or a fragment thereof, which encodes DAPK, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding DAPK may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of DAPK include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20 nucleotides in length. For a certain type of microarray, it may be preferable to use oligonucleotides which are only 7–10 nucleotides in length. The microarray may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from 2 to one million.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligonucleotides may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, LIV, mechanical or chemical bonding procedures. An array may be produced by hand or using available devices (slot blot or dot blot apparatus), materials and machines (including robotic instruments) and may contain 8, 24, 96, 384, 1536 or 6144 oligonucleotides, or any other multiple from 2 to one million which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Nat'l. Acad. Sci. 94:2150–55).

In another embodiment of the invention, the nucleic acid sequences which encode DAPK may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verna et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding DAPK on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, DAPK, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between DAPK and the agent being tested, may be measured.

Another technique for drug screening which may be used provides for high throughput screening of compounds having suitable binding affinity to the protein of interest as described in published PCT application WO84/03564. In this method, as applied to DAPK large numbers of different small test compounds are synthesized on a solid substrate, such as plastic pins or some other surface. The test compounds are reacted with DAPK, or fragments thereof, and washed. Bound DAPK is then detected by methods well known in the art. Purified DAPK can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding DAPK specifically compete with a test compound for binding DAPK. In this manner, the antibodies can be used to detect the presence of any peptide which shares one or more antigenic determinants with DAPK.

In additional embodiments, the nucleotide sequences which encode DAPK may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the TMLR3DT01 cDNA library, from which Incyte Clone 402339 was isolated, is described. Preparation and sequencing of cDNAs in libraries in the LIFESEQ database have varied over time, and the gradual changes involved use of particular kits, plasmids, and machinery available at the particular time the library was made and analyzed.

I TMLR3DT01 cDNA Library Construction

The TMLR3DT01 cDNA library was constructed from normal peripheral blood T-lymphocytes obtained from two unrelated Caucasian males aged 25 and 29 years. This library represents a mixture of allogeneically stimulated human T cell populations obtained from FICOLL/HYPAQUE gradient purified buffy coats. The cells from the two different donors (not typed for HLA alleles) were incubated at a density of $1 \times 10^6$/ml, cultured for 96 hours in DME containing 10% human serum, washed in PBS, scraped and lyzed immediately in buffer containing guanidinium isothiocyanate. The lysate was extracted twice with a mixture of phenol and chloroform, pH 8.0 and centrifuged over a CsCI cushion using an Beckman SW28 rotor in a L8-70M ultracentrifuge (Beckman Instruments). The RNA was precipitated using 0.3 M sodium acetate and 2.5 volumes of ethanol, resuspended in water and DNase treated for 15 min at 37° C. The total RNA was isolated using the Qiagen Oligotex kit (QIAGEN Inc, Chatsworth Calif.). B lymphocytes were not removed, and some contaminating macrophages may also have been present.

Stratagene (La Jolla Calif.) used the total RNA to construct a custom cDNA library. First strand cDNA synthesis was accomplished using an oligo d(T) primer/linker which also contained an XhoI restriction site. Second strand synthesis was performed using a combination of DNA polymerase 1, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 800 bp in size. The size-selected cDNAs were inserted into the LAMB-DAZAP vector system (Stratagene); and the vector which contains the PBLUESCRIPT phagemid (Stratagene) was transformed into cells of E. coli, strain XL1-BLUEMRF (Stratagene).

The phagemid forms of individual cDNA clones were obtained by the in vivo excision process. Enzymes from both BLUESCRIPT plagemid and a co-transformed f1 helper phage nicked the DNA, initiated new DNA synthesis, and created the smaller, single-stranded, circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of CDNA Clones Plasmid DNA was released from the cells and purified using the MINIPREP kit (Catalogue # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, Gibco/BRL, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to Tris buffer was not routinely performed. After the last step in the protocol, samples were transferred to a Beckman 96-well block for storage.

The cDNAs were sequenced by the method of Sanger F and AR Coulson (1 975; J Mol Biol 94:441f), using a Hamilton MICROLAB 2200 (Hamilton, Reno Nev.,) in combination with four Peltier thermal cyclers (PTC200 from MJ Research, Watertown Mass.) and Applied Biosystems 377 or 373 DNA sequencing systems (Perkin Elmer) and reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology. The relevant database for a particular match were reported as GIxxx±p (where xxx is pri, rod, etc., and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques use BLAST to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding DAPK occurs. Abundance and percent abundance are also reported. Abundance directly reflects the number of times a particular transcript is represented in a cDNA library, and percent abundance is abundance divided by the total number of sequences examined in the cDNA library.

V Extension of DAPK Encoding Polynucleotides

The nucleic acid sequence of an Incyte Clone disclosed in the Sequence Listing was used to design oligonucleotide primers for extending a partial nucleotide sequence to fill length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 primer analysis software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK DNA gel purification (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:8–14 are used to obtain 5' regulatory sequences using the procedure above, oligonucleotides designed for 5' extension, and an appropriate genomic library.

VI Labeling and Use of Individual Hybridization Probes

Hybridization probes derived from SEQ ID NOs:8–14 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 primer analysis software (National Biosciences), labeled by combining 50 pmol of each oligomer and 250 µCi of [$\lambda$-$^{32}$P] adenosine triphosphate (Amersham) and T4 polynucleotide kinase (DuPont NEN®, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba I, or Pvu II; DuPont NEN®).

The DNA from each digest is fractionated on a 0.7 percent agarose gel and transferred to nylon membranes (NYTRA PLUS membrane, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR autoradiography film (Kodak, Rochester, N.Y.) is exposed to the blots or the blots are placed in a cassette (Molecular Dynamics, Sunnyvale, Calif.) for several hours, hybridization patterns are compared visually.

VII Microarrays

To produce oligonucleotides for a microarray, SEQ ID NO:8–14 were examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identified approximately 20 sequence-specific oligonucleotides of 20 nucleotides in length (20-mers). A matched set of oligonucleotides was created in which one nucleotide in the center of each sequence was altered. This process was repeated for each gene in the microarray, and double sets of twenty 20 mers were synthesized and arranged on the surface of the silicon chip using a light-directed chemical process (Chee, M. et al., PCT/WO95/11995, incorporated herein by reference).

In the alternative, a chemical coupling procedure and an ink jet device were used to synthesize oligomers on the surface of a substrate (Baldeschweiler, J. D. et al., PCT/WO95/25116, incorporated herein by reference). In another alternative, a "gridded" array analogous to a dot (or slot) blot was used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray was washed to remove non-hybridized probes, and a scanner was used to determine the levels and patterns of fluorescence. The scanned images were examined to determine degree of complementarity and the relative abundance/expression level of each oligonucleotide sequence in the micro-array.

VIII Complementary Polynucleotides

Sequence complementary to the sequence encoding DAPK, or any part thereof, is used to detect, decrease or inhibit expression of naturally occurring DAPK. Although use of oligonucleotides comprising from about 15 to about 30 base-pairs is described, essentially the same procedure is used with smaller or larger sequence fragments. Appropriate oligonucleotides are designed using OLIGO 4.06 primer analysis software and the coding sequence of DAPK, SEQ ID NOs:8–14. To inhibit transcription, a complementary oligonucleotide is designed from the most unique 5' sequence and used to prevent promoter binding to the coding sequence. To inhibit translation, a complementary oligonucleotide is designed to prevent ribosomal binding to the transcript encoding DAPK.

IX Expression of DAPK

Expression of DAPK is accomplished by subcloning the cDNAs into appropriate vectors and transforming the vectors into host cells. In this case, the cloning vector is also used to express DAPK in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of DAPK into the bacterial growth media which can be used directly in the following assay for activity.

X Demonstration of DAPK Activity

DAPK activity may be measured by phosphorylation of a protein substrate using gamma-labeled $^{32}$P-ATP and quantitation of the incorporated radioactivity using a gamma radioisotope counter. DAPK is incubated with the protein substrate, $^{32}$P-ATP, and a kinase buffer. The $^{32}$P incorporated into the substrate is then separated from free $^{32}$P-ATP by electrophoresis and the incorporated $^{32}$P is counted. The amount of $^{32}$P recovered is proportional to the activity of DAPK in the assay. A determination of the specific amino acid residues phosphorylated is made by phosphoamino acid analysis of the hydrolyzed protein.

XI Production of DAPK Specific Antibodies

DAPK that is substantially purified using PAGE electrophoresis (Sambrook, supra), or other purification techniques, is used to immunize rabbits and to produce antibodies using standard protocols. The amino acid sequence deduced from SEQ ID NOs:8–14 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems peptide synthesizer model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring DAPK Using Specific Antibodies

Naturally occurring or recombinant DAPK is substantially purified by immunoaffinity chromatography using antibodies specific for DAPK. An immunoaffinity column is constructed by covalently coupling DAPK antibody to an activated chromatographic resin, such as CNBr-activated SEPHAROSE (Pharmacia & Upjohn). After the coupling, the resin is blocked and washed according to the manufacturer's instructions.

Media containing DAPK is passed over the immunoaffinity column, and the column is washed under conditions that allow the preferential absorbance of DAPK (e.g., high ionic strength buffers in the presence of detergent). The column is eluted under conditions that disrupt antibody/protein binding (eg, a buffer of pH 2–3 or a high concentration of a chaotrope, such as urea or thiocyanate ion), and DAPK is collected.

XIII Identification of Molecules Which Interact with DAPK

DAPK or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled DAPK, washed and any wells with labeled DAPK complex are assayed. Data obtained using different concentrations of DAPK are used to calculate values for the number, affinity, and association of DAPK with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified human disease associated protein kinase (DAPK) comprising an amino acid sequence selected from the group consisting of:
   a) SEQ ID NOs:1, 2, 4, 5, 6, or 7, and
   b) a naturally-occurring amino acid sequence having at least 90% sequence identity over the complete sequence of SEQ ID NOs:1, 2, 4, and 7, and which retains protein kinase activity.

2. A composition comprising a purified polypeptide of claim 1 in conjunction with a pharmaceutically acceptable carrier.

3. An isolated polypeptide having a sequence selected from the group consisting of SEQ ID NOs:1, 2, 4, 5, 6, and 7.

4. A method for screening a compound for effectiveness as an agonist of a human disease associated protein kinase (DAPK) of claim 1, the method comprising:
   a) exposing a sample comprising a kinase of claim 1 to a compound, and
   b) detecting an increase in kinase activity in the sample.

5. A method for screening a compound for effectiveness as an antagonist of a human disease associated protein kinase (DAPK) of claim 1, the method comprising:
   a) exposing a sample comprising a kinase of claim 1 to a compound, and
   b) detecting a decrease in kinase activity in the sample.

6. A method of making a polyclonal antibody, the method comprising:
   a) immunizing an animal with a polypeptide of claim 1 under conditions to elicit an antibody response;
   b) isolating animal antibodies; and
   c) screening the isolated antibodies with the polypeptide thereby identifying a polyclonal antibody that binds specifically to the polypeptide.

7. A method of making a monoclonal antibody, the method comprising:
   a) immunizing an animal with a polypeptide of claim 1 under conditions to elicit an antibody response;
   b) isolating antibody producing cells from the animal;
   c) fusing the antibody producing cells with immortalized cells in culture to form monoclonal antibody-producing hybridoma cells;
   d) culturing the hybridoma cells; and
   e) isolating from the culture monoclonal antibodies which bind specifically to the polypeptide.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 685 amino acids
      (B) TYPE: amino acid
      (C) STRANDEDNESS: single
      (D) TOPOLOGY: linear (vii) IMMEDIATE SOURCE:
      (A) LIBRARY: HUVENOB01
      (B) CLONE: 39043

(xi) SEQUENCE DESCRIPTION: SEQ ID NO:1:

```
Met Glu Leu Leu Arg Thr Ile Thr Tyr Gln Pro Ala Ala Ser Thr Lys
 1               5                  10                  15

Met Cys Glu Gln Ala Leu Gly Lys Gly Cys Gly Ala Asp Ser Lys Lys
            20                  25                  30

Lys Arg Pro Pro Gln Pro Pro Glu Glu Ser Gln Pro Pro Gln Ser Gln
        35                  40                  45

Ala Gln Val Pro Pro Ala Ala Pro His His His His His Ser His
    50                  55                  60

Ser Gly Pro Glu Ile Ser Arg Ile Ile Val Asp Pro Thr Thr Gly Lys
65                  70                  75                  80

Arg Tyr Cys Arg Gly Lys Val Leu Gly Lys Gly Gly Phe Ala Lys Cys
                85                  90                  95

Tyr Glu Met Thr Asp Leu Thr Asn Asn Lys Val Tyr Ala Ala Lys Ile
            100                 105                 110

Ile Pro His Ser Arg Val Ala Lys Pro His Gln Arg Glu Lys Ile Asp
        115                 120                 125

Lys Glu Ile Glu Leu His Arg Ile Leu His His Lys His Val Val Gln
    130                 135                 140

Phe Tyr His Tyr Phe Glu Asp Lys Glu Asn Ile Tyr Ile Leu Leu Glu
145                 150                 155                 160

Tyr Cys Ser Arg Arg Ser Met Ala His Ile Leu Lys Ala Arg Lys Val
                165                 170                 175

Leu Thr Glu Pro Glu Val Arg Tyr Tyr Leu Arg Gln Ile Val Ser Gly
            180                 185                 190

Leu Lys Tyr Leu His Glu Gln Glu Ile Leu His Arg Asp Leu Lys Leu
        195                 200                 205

Gly Asn Phe Phe Ile Asn Glu Ala Met Glu Leu Lys Val Gly Asp Phe
    210                 215                 220

Gly Leu Ala Ala Arg Leu Glu Pro Leu Glu His Arg Arg Arg Thr Ile
225                 230                 235                 240

Cys Gly Thr Pro Asn Tyr Leu Ser Pro Glu Val Leu Asn Lys Gln Gly
                245                 250                 255

His Gly Cys Glu Ser Asp Ile Trp Ala Leu Gly Cys Val Met Tyr Thr
            260                 265                 270

Met Leu Leu Gly Arg Pro Pro Phe Glu Thr Thr Asn Leu Lys Glu Thr
        275                 280                 285

Tyr Arg Cys Ile Arg Glu Ala Arg Tyr Thr Met Pro Ser Ser Leu Leu
    290                 295                 300
```

```
Ala Pro Ala Lys His Leu Ile Ala Ser Met Leu Ser Lys Asn Pro Glu
305                 310                 315                 320

Asp Arg Pro Ser Leu Asp Asp Ile Ile Arg His Asp Phe Leu Gln
            325                 330                 335

Gly Phe Thr Pro Asp Arg Leu Ser Ser Cys Cys His Thr Val Pro
            340                 345                 350

Asp Phe His Leu Ser Ser Pro Ala Lys Asn Phe Phe Lys Lys Ala Ala
            355                 360                 365

Ala Ala Leu Phe Gly Gly Lys Lys Asp Lys Ala Arg Tyr Ile Asp Thr
370                 375                 380

His Asn Arg Val Ser Lys Glu Asp Glu Asp Ile Tyr Lys Leu Arg His
385                 390                 395                 400

Asp Leu Lys Lys Thr Ser Ile Thr Gln Gln Pro Ser Lys His Arg Thr
                405                 410                 415

Asp Glu Glu Leu Gln Pro Pro Thr Thr Val Ala Arg Ser Gly Thr
            420                 425                 430

Pro Ala Val Glu Asn Lys Gln Gln Ile Gly Asp Ala Ile Arg Met Ile
            435                 440                 445

Val Arg Gly Thr Leu Gly Ser Cys Ser Ser Ser Glu Cys Leu Glu
450                 455                 460

Asp Ser Thr Met Gly Ser Val Ala Asp Thr Val Ala Arg Val Leu Arg
465                 470                 475                 480

Gly Cys Leu Glu Asn Met Pro Glu Ala Asp Cys Ile Pro Lys Glu Gln
                485                 490                 495

Leu Ser Thr Ser Phe Gln Trp Val Thr Lys Trp Val Asp Tyr Ser Asn
            500                 505                 510

Lys Tyr Gly Phe Gly Tyr Gln Leu Ser Asp His Thr Val Gly Val Leu
            515                 520                 525

Phe Asn Asn Gly Ala His Met Ser Leu Leu Pro Asp Lys Lys Thr Ala
            530                 535                 540

His Tyr Tyr Ala Glu Leu Gly Gln Cys Ser Val Phe Pro Ala Thr Asp
545                 550                 555                 560

Ala Pro Glu Gln Phe Ile Ser Gln Val Thr Val Leu Lys Tyr Phe Ser
                565                 570                 575

His Tyr Met Glu Glu Asn Leu Met Asp Gly Gly Asp Leu Pro Ser Val
            580                 585                 590

Thr Asp Ile Arg Arg Pro Arg Leu Tyr Leu Leu Gln Trp Leu Lys Ser
            595                 600                 605

Asp Lys Ala Leu Met Met Leu Phe Asn Asp Gly Thr Phe Gln Val Asn
610                 615                 620

Phe Tyr His Asp His Thr Lys Ile Ile Cys Ser Gln Asn Glu Glu
625                 630                 635                 640

Tyr Leu Leu Thr Tyr Ile Asn Glu Asp Arg Ile Ser Thr Thr Phe Arg
                645                 650                 655

Leu Thr Thr Leu Leu Met Ser Gly Cys Ser Ser Glu Leu Lys Asn Arg
            660                 665                 670

Met Glu Tyr Ala Leu Asn Met Leu Leu Gln Arg Cys Asn
675                 680                 685

(2) INFORMATION FOR SEQ ID NO:2:

(i) SEQUENCE CHARACTERISTICS:
        (A) LENGTH: 448 amino acids
        (B) TYPE: amino acid
        (C) STRANDEDNESS: single
```

(D) TOPOLOGY: linear (vii) IMMEDIATE SOURCE:
          (A) LIBRARY: TBLYNOT01
          (B) CLONE: 40194

(xi) SEQUENCE DESCRIPTION: SEQ ID NO:2:

```
Met Pro Pro Lys Arg Asn Glu Lys Tyr Lys Leu Pro Ile Pro Phe Pro
  1               5                  10                  15

Glu Gly Lys Val Leu Asp Asp Met Glu Gly Asn Gln Trp Val Leu Gly
                 20                  25                  30

Lys Lys Ile Gly Ser Gly Gly Phe Gly Leu Ile Tyr Leu Ala Phe Pro
             35                  40                  45

Thr Asn Lys Pro Glu Lys Asp Ala Arg His Val Val Lys Val Glu Tyr
         50                  55                  60

Gln Glu Asn Gly Pro Leu Phe Ser Glu Leu Lys Phe Tyr Gln Arg Val
 65                  70                  75                  80

Ala Lys Lys Asp Cys Ile Lys Lys Trp Ile Glu Arg Lys Gln Leu Asp
                 85                  90                  95

Tyr Leu Gly Ile Pro Leu Phe Tyr Gly Ser Gly Leu Thr Glu Phe Lys
            100                 105                 110

Gly Arg Ser Tyr Arg Phe Met Val Met Glu Arg Leu Gly Ile Asp Leu
            115                 120                 125

Gln Lys Ile Ser Gly Gln Asn Gly Thr Phe Lys Lys Ser Thr Val Leu
130                 135                 140

Gln Leu Gly Ile Arg Met Leu Asp Val Leu Glu Tyr Ile His Glu Asn
145                 150                 155                 160

Glu Tyr Val His Gly Asp Val Lys Ala Ala Asn Leu Leu Leu Gly Tyr
                165                 170                 175

Lys Asn Pro Asp Gln Val Tyr Leu Ala Asp Tyr Gly Leu Ser Tyr Arg
            180                 185                 190

Tyr Cys Pro Asn Gly Asn His Lys Gln Tyr Gln Glu Asn Pro Arg Lys
            195                 200                 205

Gly His Asn Gly Thr Ile Glu Phe Thr Ser Leu Asp Ala His Lys Gly
        210                 215                 220

Val Gly Glu Ile Ala Gln Phe Leu Val Cys Ala His Ser Leu Ala Tyr
225                 230                 235                 240

Asp Glu Lys Pro Asn Tyr Gln Ala Leu Lys Lys Ile Leu Asn Pro His
                245                 250                 255

Gly Ile Pro Leu Gly Pro Leu Asp Phe Ser Thr Lys Gly Gln Ser Ile
            260                 265                 270

Asn Val His Thr Pro Asn Ser Gln Lys Val Asp Ser Gln Lys Ala Ala
            275                 280                 285

Thr Lys Gln Val Asn Lys Ala His Asn Arg Leu Ile Glu Lys Lys Val
290                 295                 300

His Ser Glu Arg Ser Ala Glu Ser Cys Ala Thr Trp Lys Val Gln Lys
305                 310                 315                 320

Glu Glu Lys Leu Ile Gly Leu Met Asn Asn Glu Ala Ala Gln Glu Ser
                325                 330                 335

Thr Arg Arg Arg Gln Lys Tyr Gln Glu Ser Gln Glu Pro Leu Asn Glu
            340                 345                 350

Val Asn Ser Phe Pro Gln Lys Ile Ser Tyr Thr Gln Phe Pro Asn Ser
            355                 360                 365

Phe Tyr Glu Pro His Gln Asp Phe Thr Ser Pro Asp Ile Phe Lys Lys
370                 375                 380
```

```
Ser Arg Ser Pro Ser Trp Tyr Lys Tyr Thr Ser Thr Val Ser Thr Gly
385                 390                 395                 400

Ile Thr Asp Leu Glu Ser Ser Thr Gly Leu Trp Pro Thr Ile Ser Gln
                405                 410                 415

Phe Thr Leu Ser Glu Glu Thr Asn Ala Asp Val Tyr Tyr Tyr Arg Ile
                420                 425                 430

Ile Ile Pro Val Leu Leu Met Leu Val Phe Leu Ala Leu Phe Phe Leu
                435                 440                 445

(2) INFORMATION FOR SEQ ID NO:3:

(i) SEQUENCE CHARACTERISTICS:
        (A) LENGTH: 400 amino acids
        (B) TYPE: amino acid
        (C) STRANDEDNESS: single
        (D) TOPOLOGY: linear (vii) IMMEDIATE SOURCE:
        (A) LIBRARY: TMLR3DT01
        (B) CLONE: 402339

(xi) SEQUENCE DESCRIPTION: SEQ ID NO:3:

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
                20                  25                  30

Asn Leu Val Asp Leu Gln Lys Lys Leu Glu Glu Leu Glu Leu Asp Glu
                35                  40                  45

Gln Gln Lys Lys Arg Leu Glu Ala Phe Leu Thr Gln Lys Ala Lys Val
        50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
                100                 105                 110

Asn Gln Ile Ile Arg Glu Leu Gln Val Leu His Glu Cys Asn Ser Pro
            115                 120                 125

Tyr Ile Val Gly Phe Tyr Gly Ala Phe Tyr Ser Asp Gly Glu Ile Ser
        130                 135                 140

Ile Cys Met Glu His Met Asp Gly Gly Ser Leu Asp His Leu Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
                180                 185                 190

Arg Asp Val Lys Pro Ser Asn Ile Leu Val Asn Ser Arg Gly Glu Ile
                195                 200                 205

Lys Leu Cys Asp Phe Gly Val Ser Gly Gln Leu Ile Asp Ser Met Ala
                210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Pro Asp Ala
                260                 265                 270
```

-continued

```
Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Pro Gly Arg Pro
    290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
        355                 360                 365

Ile Lys Arg Ser Glu Val Glu Val Asp Phe Ala Gly Trp Leu Cys
    370                 375                 380

Lys Thr Leu Arg Leu Asn Gln Pro Gly Thr Pro Thr Arg Thr Ala Val
385                 390                 395                 400
```

(2) INFORMATION FOR SEQ ID NO:4:

(i) SEQUENCE CHARACTERISTICS:
        (A) LENGTH: 464 amino acids
        (B) TYPE: amino acid
        (C) STRANDEDNESS: single
        (D) TOPOLOGY: linear (vii) IMMEDIATE SOURCE:
        (A) LIBRARY: SYNORAT04
        (B) CLONE: 705365

(xi) SEQUENCE DESCRIPTION: SEQ ID NO:4:

```
Met Ala Met Thr Ala Gly Thr Thr Thr Thr Phe Pro Met Ser Asn His
1               5                   10                  15

Thr Arg Glu Arg Val Thr Val Ala Lys Leu Thr Leu Glu Asn Phe Tyr
            20                  25                  30

Ser Asn Leu Ile Leu Gln His Glu Glu Arg Glu Thr Arg Gln Lys Lys
        35                  40                  45

Leu Glu Val Ala Met Glu Glu Gly Leu Ala Asp Glu Glu Lys Lys
    50                  55                  60

Leu Arg Arg Ser Gln His Ala Arg Lys Glu Thr Glu Phe Leu Arg Leu
65                  70                  75                  80

Lys Arg Thr Arg Leu Gly Leu Asp Asp Phe Glu Ser Leu Lys Val Ile
                85                  90                  95

Gly Arg Gly Ala Phe Gly Glu Val Arg Leu Val His Lys Lys Asp Thr
            100                 105                 110

Gly His Ile Tyr Ala Met Lys Ile Leu Arg Lys Ser Asp Met Leu Glu
        115                 120                 125

Lys Glu Gln Val Ala His Ile Arg Ala Glu Arg Asp Ile Leu Val Glu
    130                 135                 140

Ala Asp Gly Ala Trp Val Val Lys Met Phe Tyr Ser Phe Gln Asp Lys
145                 150                 155                 160

Arg Asn Leu Tyr Leu Ile Met Glu Phe Leu Pro Gly Gly Asp Met Met
                165                 170                 175

Thr Leu Leu Met Lys Lys Asp Thr Leu Thr Glu Glu Glu Thr Gln Phe
            180                 185                 190

Tyr Ile Ser Glu Thr Val Leu Ala Ile Asp Ala Ile His Gln Leu Gly
        195                 200                 205

Phe Ile His Arg Asp Ile Lys Pro Asp Asn Leu Leu Leu Asp Ala Lys
```

-continued

```
                  210                 215                 220
Gly His Val Lys Leu Ser Asp Phe Gly Ser Cys Thr Gly Leu Lys Lys
225                 230                 235                 240

Ala His Arg Thr Glu Phe Tyr Arg Asn Leu Thr His Asn Pro Pro Ser
                245                 250                 255

Asp Phe Ser Phe Gln Asn Met Asn Ser Lys Arg Lys Ala Glu Thr Trp
                260                 265                 270

Lys Lys Asn Arg Arg Gln Leu Ala Tyr Ser Thr Val Gly Thr Pro Asp
                275                 280                 285

Tyr Ile Ala Pro Glu Val Phe Met Gln Thr Gly Tyr Asn Lys Leu Cys
290                 295                 300

Asp Trp Trp Ser Leu Gly Val Ile Met Tyr Glu Met Leu Ile Gly Tyr
305                 310                 315                 320

Pro Pro Phe Cys Ser Glu Thr Pro Gln Glu Thr Tyr Arg Lys Val Met
                325                 330                 335

Asn Trp Lys Glu Thr Leu Val Phe Pro Pro Glu Val Pro Ile Ser Glu
                340                 345                 350

Lys Ala Lys Asp Leu Ile Leu Arg Phe Cys Ile Asp Ser Glu Asn Arg
                355                 360                 365

Ile Gly Asn Ser Gly Val Glu Glu Ile Lys Gly His Pro Phe Phe Glu
                370                 375                 380

Gly Val Asp Trp Glu His Ile Arg Glu Arg Pro Ala Ala Ile Pro Ile
385                 390                 395                 400

Glu Ile Lys Ser Ile Asp Asp Thr Ser Asn Phe Asp Asp Phe Pro Glu
                405                 410                 415

Ser Asp Ile Leu Gln Pro Val Pro Asn Thr Thr Glu Pro Asp Tyr Lys
                420                 425                 430

Ser Lys Asp Trp Val Phe Leu Asn Tyr Thr Tyr Lys Arg Phe Glu Gly
                435                 440                 445

Leu Thr Gln Arg Gly Ser Ile Pro Thr Tyr Met Lys Ala Gly Lys Leu
                450                 455                 460
```

(2) INFORMATION FOR SEQ ID NO:5:

(i) SEQUENCE CHARACTERISTICS:
        (A) LENGTH: 343 amino acids
        (B) TYPE: amino acid
        (C) STRANDEDNESS: single
        (D) TOPOLOGY: linear (vii) IMMEDIATE SOURCE:
        (A) LIBRARY: PROSNOT06
        (B) CLONE: 827431

(xi) SEQUENCE DESCRIPTION: SEQ ID NO:5:

```
Met Leu Leu Lys Lys His Thr Glu Asp Ile Ser Ser Val Tyr Glu
1               5                  10                  15

Ile Arg Glu Arg Leu Gly Ser Gly Ala Phe Ser Glu Val Val Leu Ala
                20                  25                  30

Gln Glu Arg Gly Ser Ala His Leu Val Ala Leu Lys Cys Ile Pro Lys
                35                  40                  45

Lys Ala Leu Arg Gly Lys Glu Ala Leu Val Glu Asn Glu Ile Ala Val
50                  55                  60

Leu Arg Arg Ile Ser His Pro Asn Ile Val Ala Leu Glu Asp Val His
65                  70                  75                  80

Glu Ser Pro Ser His Leu Tyr Leu Ala Met Glu Leu Val Thr Gly Gly
                85                  90                  95
```

-continued

```
Glu Leu Phe Asp Arg Ile Met Glu Arg Gly Ser Tyr Thr Glu Lys Asp
            100                 105                 110

Ala Ser His Leu Val Gly Gln Val Leu Gly Ala Val Ser Tyr Leu His
        115                 120                 125

Ser Leu Gly Ile Val His Arg Asp Leu Lys Pro Glu Asn Leu Leu Tyr
    130                 135                 140

Ala Thr Pro Phe Glu Asp Ser Lys Ile Met Val Ser Asp Phe Gly Leu
145                 150                 155                 160

Ser Lys Ile Gln Ala Gly Asn Met Leu Gly Thr Ala Cys Gly Thr Pro
                165                 170                 175

Gly Tyr Val Ala Pro Glu Leu Leu Glu Gln Lys Pro Tyr Gly Lys Ala
            180                 185                 190

Val Asp Val Trp Ala Leu Gly Val Ile Ser Tyr Ile Leu Leu Cys Gly
        195                 200                 205

Tyr Pro Pro Phe Tyr Asp Glu Ser Asp Pro Glu Leu Phe Ser Gln Ile
    210                 215                 220

Leu Arg Ala Ser Tyr Glu Phe Asp Xaa Pro Phe Trp Asp Asp Ile Ser
225                 230                 235                 240

Glu Ser Gly Lys Asp Phe Ile Arg His Leu Leu Glu Arg Asp Leu Gln
                245                 250                 255

Lys Arg Phe Thr Cys Gln Gln Ala Leu Arg Asp Leu Trp Ile Phe Trp
            260                 265                 270

Asp Thr Gly Phe Gly Arg Asp Ile Leu Gly Phe Val Ser Glu Gln Ile
        275                 280                 285

Arg Lys Asn Phe Ala Trp Thr His Trp Lys Arg Ala Phe Asn Ala Thr
    290                 295                 300

Leu Phe Leu Arg His Ile Arg Lys Leu Gly Gln Ile Pro Glu Gly Glu
305                 310                 315                 320

Gly Ala Ser Glu Gln Gly Met Xaa Arg His Ser His Xaa Gly Leu Arg
                325                 330                 335

Ala Gly Gln Pro Pro Lys Trp
            340

(2) INFORMATION FOR SEQ ID NO:6:

(i) SEQUENCE CHARACTERISTICS:
        (A) LENGTH: 412 amino acids
        (B) TYPE: amino acid
        (C) STRANDEDNESS: single
        (D) TOPOLOGY: linear (vii) IMMEDIATE SOURCE:
        (A) LIBRARY: COLNTUT03
        (B) CLONE: 1340712

(xi) SEQUENCE DESCRIPTION: SEQ ID NO:6:

Met Ile Leu Ala Ser Val Leu Arg Ser Gly Pro Gly Gly Leu Pro
1               5                   10                  15

Leu Arg Pro Leu Leu Gly Pro Ala Leu Ala Leu Arg Ala Arg Ser Thr
                20                  25                  30

Ser Ala Thr Asp Thr His His Val Glu Met Ala Arg Glu Arg Ser Lys
            35                  40                  45

Thr Val Thr Ser Phe Tyr Asn Gln Ser Ala Ile Asp Ala Ala Ala Glu
    50                  55                  60

Lys Pro Ser Val Arg Leu Thr Pro Thr Met Met Leu Tyr Ala Gly Arg
65                  70                  75                  80
```

-continued

```
Ser Gln Asp Gly Ser His Leu Leu Lys Ser Ala Arg Tyr Leu Gln Gln
                85                  90                  95

Glu Leu Pro Val Arg Ile Ala His Arg Ile Lys Gly Phe Arg Cys Leu
            100                 105                 110

Pro Phe Ile Ile Gly Cys Asn Pro Thr Ile Leu His Val His Glu Leu
        115                 120                 125

Tyr Ile Arg Ala Phe Gln Lys Leu Thr Asp Phe Pro Pro Ile Lys Asp
    130                 135                 140

Gln Ala Asp Glu Ala Gln Tyr Cys Gln Leu Val Arg Gln Leu Leu Asp
145                 150                 155                 160

Asp His Lys Asp Val Val Thr Leu Leu Ala Glu Gly Leu Arg Glu Ser
                165                 170                 175

Arg Lys His Ile Glu Asp Glu Lys Leu Val Arg Tyr Phe Leu Asp Lys
            180                 185                 190

Thr Leu Thr Ser Arg Leu Gly Ile Arg Met Leu Ala Thr His His Leu
        195                 200                 205

Ala Leu His Glu Asp Lys Pro Asp Phe Val Gly Ile Ile Cys Thr Arg
    210                 215                 220

Leu Ser Pro Lys Lys Ile Ile Glu Lys Trp Val Asp Phe Ala Arg Arg
225                 230                 235                 240

Leu Cys Glu His Lys Tyr Gly Asn Ala Pro Arg Val Arg Ile Asn Gly
                245                 250                 255

His Val Ala Ala Arg Phe Pro Phe Ile Pro Met Pro Leu Asp Tyr Ile
            260                 265                 270

Leu Pro Glu Leu Leu Lys Asn Ala Met Arg Ala Thr Met Glu Ser His
        275                 280                 285

Leu Asp Thr Pro Tyr Asn Val Pro Asp Val Val Ile Thr Ile Ala Asn
    290                 295                 300

Asn Asp Val Asp Leu Ile Ile Arg Ile Ser Asp Arg Gly Gly Gly Ile
305                 310                 315                 320

Ala His Lys Asp Leu Asp Arg Val Met Asp Tyr His Phe Thr Thr Ala
                325                 330                 335

Glu Ala Ser Thr Gln Asp Pro Arg Ile Ser Pro Leu Phe Gly His Leu
            340                 345                 350

Asp Met His Ser Gly Ala Gln Ser Gly Pro Met His Gly Phe Gly Phe
        355                 360                 365

Gly Leu Pro Thr Ser Arg Ala Tyr Ala Glu Tyr Leu Gly Gly Ser Leu
    370                 375                 380

Gln Leu Gln Ser Leu Gln Gly Ile Gly Thr Asp Val Tyr Leu Arg Leu
385                 390                 395                 400

Arg His Ile Asp Gly Arg Glu Glu Ser Phe Arg Ile
                405                 410
```

(2) INFORMATION FOR SEQ ID NO:7:

(i) SEQUENCE CHARACTERISTICS:
        (A) LENGTH: 328 amino acids
        (B) TYPE: amino acid
        (C) STRANDEDNESS: single
        (D) TOPOLOGY: linear (vii) IMMEDIATE SOURCE:
        (A) LIBRARY: PENITUT01
        (B) CLONE: 1452972

(xi) SEQUENCE DESCRIPTION: SEQ ID NO:7:

Met Leu Glu Lys Leu Glu Phe Glu Asp Glu Ala Val Glu Asp Ser Glu

```
              1               5                10               15
Ser Gly Val Tyr Met Arg Phe Met Arg Ser His Lys Cys Tyr Asp Ile
                    20                  25                  30

Val Pro Thr Ser Ser Lys Leu Val Phe Asp Thr Thr Leu Gln Val
            35                  40                  45

Lys Lys Ala Phe Phe Ala Leu Val Ala Asn Gly Val Arg Ala Ala Pro
    50                      55                  60

Leu Trp Glu Ser Lys Lys Gln Ser Phe Val Gly Met Leu Thr Ile Thr
65                      70                  75                  80

Asp Phe Ile Asn Ile Leu His Arg Tyr Tyr Lys Ser Pro Met Val Gln
                        85                  90                  95

Ile Tyr Glu Leu Glu Glu His Lys Ile Glu Thr Trp Arg Glu Leu Tyr
                100                 105                 110

Leu Gln Glu Thr Phe Lys Pro Leu Val Asn Ile Ser Pro Asp Ala Ser
            115                 120                 125

Leu Phe Asp Ala Val Tyr Ser Leu Ile Lys Asn Lys Ile His Arg Leu
    130                     135                 140

Pro Val Ile Asp Pro Ile Ser Gly Asn Ala Leu Tyr Ile Leu Thr His
145                     150                 155                 160

Lys Arg Ile Leu Lys Phe Leu Gln Leu Phe Met Ser Asp Met Pro Lys
                165                 170                 175

Pro Ala Phe Met Lys Gln Asn Leu Asp Glu Leu Gly Ile Gly Thr Tyr
                180                 185                 190

His Asn Ile Ala Phe Ile His Pro Asp Thr Pro Ile Ile Lys Ala Leu
            195                 200                 205

Asn Ile Phe Val Glu Arg Arg Ile Ser Ala Leu Pro Val Val Asp Glu
    210                     215                 220

Ser Gly Lys Val Val Asp Ile Tyr Ser Lys Phe Asp Val Ile Asn Leu
225                     230                 235                 240

Ala Ala Glu Lys Thr Tyr Asn Asn Leu Asp Ile Thr Val Thr Gln Ala
                245                 250                 255

Leu Gln His Arg Ser Gln Tyr Phe Glu Gly Val Val Lys Cys Asn Lys
                260                 265                 270

Leu Glu Ile Leu Glu Thr Ile Val Asp Arg Ile Val Arg Ala Glu Val
            275                 280                 285

His Arg Leu Val Val Asn Glu Ala Asp Ser Ile Val Gly Ile Ile
    290                     295                 300

Ser Leu Ser Asp Ile Leu Gln Ala Leu Ile Leu Thr Pro Ala Gly Ala
305                     310                 315                 320

Lys Gln Lys Glu Thr Glu Thr Glu
                325
```

(2) INFORMATION FOR SEQ ID NO:8:

(i) SEQUENCE CHARACTERISTICS:
        (A) LENGTH: 2770 base pairs
        (B) TYPE: nucleic acid
        (C) STRANDEDNESS: single
        (D) TOPOLOGY: linear (vii) IMMEDIATE SOURCE:
        (A) LIBRARY: HUVENOB01
        (B) CLONE: 39043

(xi) SEQUENCE DESCRIPTION: SEQ ID NO:8:

```
TAGTCGGCAC CAGAGGCAAG GGTGCGAGGA CCACGGCCGG CTCGGACGTG TGACCGCGCC      60
```

```
TAGGGGGTGG CAGCGGGCAG TGCGGGGCGG CAAGGCGACC ATGGAGCTTT TGCGGACTAT    120
CACCTACCAG CCAGCCGCCA GCACCAAAAT GTGCGAGCAG GCGCTGGGCA AGGGTTGCGG    180
AGCGGACTCG AAGAAGAAGC GGCCGCCGCA GCCCCCCGAG GAATCGCAGC CACCTCAGTC    240
CCAGGCGCAA GTGCCCCCGG CGGCCCCTCA CCACCATCAC CACCATTCGC ACTCGGGGCC    300
GGAGATCTCG CGGATTATCG TCGACCCCAC GACTGGGAAG CGCTACTGCC GGGGCAAAGT    360
GCTGGGAAAG GGTGGCTTTG CAAAATGTTA CGAGATGACA GATTTGACAA ATAACAAAGT    420
CTACGCCGCA AAAATTATTC CTCACAGCAG AGTAGCTAAA CCTCATCAAA GGGAAAAGAT    480
TGACAAAGAA ATAGAGCTTC ACAGAATTCT TCATCATAAG CATGTAGTGC AGTTTTACCA    540
CTACTTCGAG GACAAAGAAA ACATTTACAT TCTCTTGGAA TACTGCAGTA GAAGGTCAAT    600
GGCTCATATT TTGAAAGCAA GAAAGGTGTT GACAGAGCCA GAAGTTCGAT ACTACCTCAG    660
GCAGATTGTG TCTGGACTGA ATACCTTCA TGAACAAGAA ATCTTGCACA GAGATCTCAA     720
ACTAGGGAAC TTTTTTATTA ATGAAGCCAT GGAACTAAAA GTTGGGGACT TCGGTCTGGC    780
AGCCAGGCTA GAACCCTTGG AACACAGAAG GAGAACGATA TGTGGTACCC CAAATTATCT    840
CTCTCCTGAA GTCCTCAACA AACAAGGACA TGGCTGTGAA TCAGACATTT GGGCCCTGGG    900
CTGTGTAATG TATACAATGT TACTAGGGAG GCCCCCATTT GAAACTACAA ATCTCAAAGA    960
AACTTATAGG TGCATAAGGG AAGCAAGGTA TACAATGCCG TCCTCATTGC TGGCTCCTGC   1020
CAAGCACTTA ATTGCTAGTA TGTTGTCCAA AAACCCAGAG GATCGTCCCA GTTTGGATGA   1080
CATCATTCGA CATGACTTTT TTTTGCAGGG CTTCACTCCG GACAGACTGT CTTCTAGCTG   1140
TTGTCATACA GTTCCAGATT TCCACTTATC AAGCCCAGCT AAGAATTTCT TTAAGAAAGC   1200
AGCTGCTGCT CTTTTTGGTG GCAAAAAAGA CAAAGCAAGA TATATTGACA CACATAATAG   1260
AGTGTCTAAA GAAGATGAAG ACATCTACAA GCTTAGGCAT GATTTGAAAA AGACTTCAAT   1320
AACTCAGCAA CCCAGCAAAC ACAGGACAGA TGAGGAGCTC CAGCCACCTA CCACCACAGT   1380
TGCCAGGTCT GGAACACCCG CAGTAGAAAA CAAGCAGCAG ATTGGGGATG CTATTCGGAT   1440
GATAGTCAGA GGGACTCTTG GCAGCTGTAG CAGCAGCAGT GAATGCCTTG AAGACAGTAC   1500
CATGGGAAGT GTTGCAGACA CAGTGGCAAG GGTTCTTCGG GGATGTCTGG AAAACATGCC   1560
GGAAGCTGAT TGCATTCCCA AAGAGCAGCT GAGCACATCA TTTCAGTGGG TCACCAAATG   1620
GGTTGATTAC TCTAACAAAT ATGGCTTTGG GTACCAGCTC TCAGACCACA CCGTCGGTGT   1680
CCTTTTCAAC AATGGTGCTC ACATGAGCC CCTTCCAGAC AAAAAAACAG CTCACTATTA    1740
CGCAGAGCTT GGCCAATGCT CAGTTTTCCC AGCAACAGAT GCTCCTGAGC AATTTATTAG   1800
TCAAGTGACG GTGCTGAAAT ACTTTTCTCA TTACATGGAG GAGAACCTCA TGGATGGTGG   1860
AGATCTGCCT AGTGTTACTG ATATTCGAAG ACCTCGGCTC TACCTCCTTC AGTGGCTAAA   1920
ATCTGATAAG GCCCTAATGA TGCTCTTTAA TGATGGCACC TTTCAGGTGA ATTTCTACCA   1980
TGATCATACA AAAATCATCA TCTGTAGCCA AAATGAAGAA TACCTTCTCA CCTACATCAA   2040
TGAGGATAGG ATATCTACAA CTTTCAGGCT GACAACTCTG CTGATGTCTG GCTGTTCATC   2100
AGAATTAAAA AATCGAATGG AATATGCCCT GAACATGCTC TTACAAAGAT GTAACTGAAA   2160
GACTTTTCGA ATGGACCCTA TGGGACTCCT CTTTTCCACT GTGAGATCTA CAGGGAAGCC   2220
AAAAGAATGA TCTAGAGTAT GTTGAAGAAG ATGGACATGT GGTGGTACGA AAACAATTCC   2280
CCTGTGGCCT GCTGGACTGG GTGGAACCAG AACAGGCTAA GCATACAGTT TCTTGACTTT   2340
GGACAATCCA AGAGTGAACC AGAATGCAGT TTTCCTTGAG ATACCTGTTT TAAAAGGTTT   2400
TTCAGACAAT TTTGCAGAAA GGTGCATTGA TTCTTAAATT CTCTCTGTTG AGAGCATTTC   2460
```

```
AGCCAGAGGA CTTTGGAACT GTGAATATAC TTCCTGAAGG GGAGGGAGAA GGGAGGAAGC    2520

TCCCATGTTG TTTAAAGGCT GTAATTGGAG CAGCTTTTGG CTGCGTAACT GTGAACTATG    2580

GCCATATATA ATTTTTTTTC ATTAATTTTT GAAGATACTT GTGGCTGGAA AAGTGCATTC    2640

CTTGTTAATA AACTTTTTAT TTATTACAGC CCAAAGAGCA GTATTTATTA TCAAAATGTC    2700

TTTTTTTTTA TGTTGACCAT TTTAAACCGT TGGCAATAAA GAGTATGAAA ACGCAGAAAA    2760

AAAAAAAAAA                                                          2770
```

(2) INFORMATION FOR SEQ ID NO:9:

(i) SEQUENCE CHARACTERISTICS:
        (A) LENGTH: 1593 base pairs
        (B) TYPE: nucleic acid
        (C) STRANDEDNESS: single
        (D) TOPOLOGY: linear (vii) IMMEDIATE SOURCE:
        (A) LIBRARY: TBLYNOT01
        (B) CLONE: 40194

(xi) SEQUENCE DESCRIPTION: SEQ ID NO:9:

```
CTAGGCGTCC CCTTCTACTC ACGTTTGCCA AAAGCGGGTC CGACGTGTTA GCGGAAAAAA      60

GTGATGCCAC CAAAAAGAAA TGAAAAATAC AAACTTCCTA TTCCATTTCC AGAAGGCAAG     120

GTTCTGGATG ATATGGAAGG CAATCAGTGG GTACTGGGCA AGAAGATTGG CTCTGGAGGA     180

TTTGGATTGA TATATTTAGC TTTCCCCACA AATAAACCAG AGAAAGATGC AAGACATGTA     240

GTAAAAGTGG AATATCAAGA AAATGGCCCG TTATTTTCAG AACTTAAATT TTATCAGAGA     300

GTTGCAAAAA AAGACTGTAT CAAAAAGTGG ATAGAACGCA AACAACTTGA TTATTTAGGA     360

ATTCCTCTGT TTTATGGATC TGGTCTGACT GAATTCAAGG GAAGAAGTTA CAGATTTATG     420

GTAATGGAAA GACTAGGAAT AGATTTACAG AAGATCTCAG GCCAGAATGG TACCTTTAAA     480

AAGTCAACTG TCCTGCAATT AGGTATCCGA ATGTTGGATG TACTGGAATA TATACATGAA     540

AATGAATATG TTCATGGTGA TGTAAAAGCA GCAAATCTAC TTTTGGGTTA CAAAAATCCA     600

GACCAGGTTT ATCTTGCAGA TTATGGACTT TCCTACAGAT ATTGTCCCAA TGGGAACCAC     660

AAACAGTATC AGGAAAATCC TAGAAAAGGC CATAATGGGA CAATAGAGTT TACCAGCTTG     720

GATGCCCACA AGGGAGTAGG TGAAATAGCC CAATTTTTGG TATGTGCTCA TAGTTTAGCA     780

TATGATGAAA AGCCAAACTA TCAAGCCCTC AAGAAAATTT TGAACCCTCA TGGAATACCT     840

TTAGGACCAC TGGACTTTTC CACAAAAGGA CAGAGTATAA ATGTCCATAC TCCAAACAGT     900

CAAAAAGTTG ATTCACAAAA GGCTGCAACA AAGCAAGTCA ACAAGGCACA CAATAGGTTA     960

ATCGAAAAAA AAGTCCACAG TGAGAGAAGC GCTGAGTCCT GTGCAACATG GAAAGTGCAG    1020

AAAGAGGAGA AACTGATTGG ATTGATGAAC AATGAAGCAG CTCAGGAAAG CACAAGGAGA    1080

AGACAGAAAT ATCAAGAGTC TCAAGAACCT TTGAATGAAG TAAACAGTTT CCCACAAAAA    1140

ATCAGCTATA CACAATTCCC AAACTCATTT TATGAGCCTC ATCAAGATTT TACCAGTCCA    1200

GATATATTCA AGAAGTCAAG ATCTCCATCT TGGTATAAAT ACACTTCCAC AGTCAGCACG    1260

GGGATCACAG ACTTAGAAAG TTCAACTGGA CTTTGGCCTA CAATTTCCCA GTTTACTCTT    1320

AGTGAAGAGA CAAACGCAGA TGTTTATTAT TATCGCATCA TCATACCTGT CCTTTTGATG    1380

TTAGTATTTC TTGCTTTATT TTTTCTCTGA AGATGATACC AAAATTCCTT TTGATAATTT    1440

TTTAAGTTTC CAGCTCTTCA CCGAAATGTT GTATTCTTAT TTCAGTGTTT CCTTCCAGAC    1500

ATTTTTAAGG TAATTGGCTT TAAAAAGAGA ACATATTTTA ACAAAGTTTG TGGACACTCT    1560
```

AAAAAATAAA ATTGCTTTGT ACTAGAAAAA AAA    1593

(2) INFORMATION FOR SEQ ID NO:10:

(i) SEQUENCE CHARACTERISTICS:
       (A) LENGTH: 1504 base pairs
       (B) TYPE: nucleic acid
       (C) STRANDEDNESS: single
       (D) TOPOLOGY: linear (vii) IMMEDIATE SOURCE:
       (A) LIBRARY: TMLR3DT01
       (B) CLONE: 402339

(xi) SEQUENCE DESCRIPTION: SEQ ID NO:10:

CCGGCCCGCG GAGCCCCGAT GCTGGCCCGG AGGAAGCCGG TGCTGCCGGC GCTCACCATC    60

AACCCTACCA TCGCCGAGGG CCCATCCCCT ACCAGCGAGG GCGCCTCCGA GGCAAACCTG    120

GTGGACCTGC AGAAGAAGCT GGAGGAGCTG GAACTTGACG AGCAGCAGAA GAAGCGGCTG    180

GAAGCCTTTC TCACCCAGAA AGCCAAGGTC GGCGAACTCA AGACGATGA CTTCGAAAGG     240

ATCTCAGAGC TGGGCGCGGG CAACGGCGGG GTGGTCACCA AAGTCCAGCA CAGACCCTCG    300

GGCCTCATCA TGGCCAGGAA GCTGATCCAC CTTGAGATCA AGCCGGCCAT CCGGAACCAG    360

ATCATCCGCG AGCTGCAGGT CCTGCACGAA TGCAACTCGC CGTACATCGT GGGCTTCTAC    420

GGGGCCTTCT ACAGTGACGG GGAGATCAGC ATTTGCATGG AACACATGGA CGGCGGCTCC    480

CTGGACCATC TGCTGAAAGA GGCCAAGAGG ATTCCCGAGG AGATCCTGGG GAAAGTCAGC    540

ATCGCGGTTC TCCGGGGCTT GGCGTACCTC CGAGAGAAGC ACCAGATCAT GCACCGAGAT    600

GTGAAGCCCT CCAACATCCT CGTGAACTCT AGAGGGGAGA TCAAGCTGTG TGACTTCGGG    660

GTGAGCGGCC AGCTCATCGA CTCCATGGCC AACTCCTTCG TGGGCACGCG CTCCTACATG    720

GCTCCGGAGC GGTTGCAGGG CACACATTAC TCGGTGCAGT CGGACATCTG GAGCATGGGC    780

CTGTCCCTGG TGGAGCTGGC CGTCGGAAGG TACCCCATCC CCCGCCCGA CGCCAAAGAG     840

CTGGAGGCCA TCTTTGGCCG GCCCGTGGTC GACGGGGAAG AAGGAGAGCC TCACAGCATC    900

TCGCCTCGGC CGAGGCCCCC CGGGCGCCCC GTCAGCGGTC ACGGGATGGA TAGCCGGCCT    960

GCCATGGCCA TCTTTGAACT CCTGGACTAT ATTGTGAACG AGCCACCTCC TAAGCTGCCC    1020

AACGGTGTGT TCACCCCCGA CTTCCAGGAG TTTGTCAATA AATGCCTCAT CAAGAACCCA    1080

GCGGAGCGGG CGGACCTGAA GATGCTCACA AACCACACCT TCATCAAGCG GTCCGAGGTG    1140

GAAGAAGTGG ATTTTGCCGG CTGGTTGTGT AAAACCCTGC GGCTGAACCA GCCCGGCACA    1200

CCCACGCGCA CCGCCGTGTG ACAGTGGCCG GGCTCCCTGC GTCCCGCTGG TGACCTGCCC    1260

ACCGTCCCTG TCCATGCCCC GCCCTTCCAG CTGAGGACAG GCTGGCGCCT CCACCCACCC    1320

TCCTGCCTCA CCCCTGCGGA GAGCACCGTG GCGGGGCGAC AGCGCATGCA GGAACGGGGG    1380

TCTCCTCTCC TGCCCGTCCT GGCCGGGGTG CCTCTGGGGA CGGGCGACGC TGCTGTGTGT    1440

GGTCTCAGAG GCTCTGCTTC CTTAGGTTAC AAAACAAAAC AGGGAGAGAA AAAGCAAAAA    1500

AAAA    1504

(2) INFORMATION FOR SEQ ID NO:11:

(i) SEQUENCE CHARACTERISTICS:
       (A) LENGTH: 1935 base pairs
       (B) TYPE: nucleic acid
       (C) STRANDEDNESS: single
       (D) TOPOLOGY: linear (vii) IMMEDIATE SOURCE:
    (A) LIBRARY: SYNORAT04
    (B) CLONE: 705365

(xi) SEQUENCE DESCRIPTION: SEQ ID NO:11:

```
GCGGAGGCTG AGCCGGCCGC GGGCGCGACC GGAGGCAGTT TCCGTTACTA TGGCAATGAC    60
GGCAGGGACT ACAACAACCT TTCCTATGAG CAACCATACC CGGGAAAGAG TGACTGTAGC   120
CAAGCTCACA TTGGAGAATT TTTATAGCAA CCTAATTTTA CAGCATGAAG AGAGAGAAAC   180
CAGGCAGAAG AAATTAGAAG TGGCCATGGA AGAAGAAGGA TTAGCAGATG AAGAGAAAAA   240
GTTACGTCGA TCACAACACG CTCGCAAAGA AACAGAGTTC TTACGGCTCA AAAGGACCAG   300
ACTTGGCTTG GATGACTTTG AGTCTCTGAA AGTTATAGGA AGAGGAGCTT TTGGAGAGGT   360
GCGGTTGGTC CACAAAAAAG ATACAGGCCA TATCTATGCA ATGAAGATAT TGAGAAAGTC   420
TGATATGCTT GAAAAAGAGC AGGTGGCCCA TATCCGAGCA GAAAGAGATA TTTTGGTAGA   480
AGCAGATGGT GCCTGGGTGG TGAAGATGTT TTACAGTTTT CAGGATAAGA GGAATCTTTA   540
TCTAATCATG GAATTTCTCC CTGGAGGTGA CATGATGACA TTGCTAATGA AGAAAGACAC   600
CTTGACAGAA GAGGAAACAC AGTTCTACAT TCAGAGACT GTTCTGGCAA TAGATGCGAT   660
CCACCAGTTG GGTTTCATCC ATCGGGATAT TAAGCCAGAC AACCTTTTAT TGGATGCCAA   720
GGGTCATGTA AAATTATCTG ATTTTGGTTC ATGTACGGGA TTAAAGAAAG CTCACAGGAC   780
TGAATTTTAT AGAAATCTCA CACACAACCC ACCAAGTGAC TTCTCATTTC AGAACATGAA   840
CTCAAAGAGG AAAGCAGAAA CTTGGAAGAA GAACAGGAGA CAACTGGCAT ATTCCACAGT   900
TGGGACACCA GATTACATTG CTCCAGAAGT ATTCATGCAG ACTGGTTACA CAAATTGTG   960
TGACTGGTGG TCTTTGGGAG TGATTATGTA TGAAATGCTA ATAGGATATC CACCTTTCTG  1020
CTCTGAAACA CCTCAAGAAA CATACAGAAA AGTGATGAAC TGGAAAGAAA CTCTGGTATT  1080
TCCTCCAGAG GTACCTATAT CTGAGAAAGC CAAGGACTTA ATTCTCAGAT TTTGTATTGA  1140
TTCTGAAAAC AGAATTGGAA ATAGTGGAGT AGAAGAAATA AAAGGTCATC CCTTTTTTGA  1200
AGGTGTCGAC TGGGAGCACA TAAGGGAAAG GCCAGCAGCA ATCCCTATAG AAATCAAAAG  1260
CATTGATGAT ACTTCAAATT TTGATGACTT CCCTGAATCT GATATTTTAC AACCAGTGCC  1320
AAATACCACA GAACCGGACT ACAAATCCAA AGACTGGGTT TTTCTCAATT ATACCTATAA  1380
AAGGTTTGAA GGGTTGACTC AACGTGGCTC TATCCCCACC TACATGAAAG CTGGGAAGTT  1440
ATGAATGAAG ATAACATTCA CCCATAACCA AGAGAACTCA GGTAGCTGCA TCACCAGGCT  1500
TGCTTGGCGT AGATAACAAT ACACTGAAAT ACTCCTGAAG ATGGTGGTGC TTATTGACTA  1560
CAAGAGGAAA TTCTACAGGA TTAGGATTTC TAAGACTACT ATAGGAATTG GTTGGCAGTG  1620
CCAGCTGGCT CTTTTTTTTA ATATTTTATT ATTTTTGTTA ACTTTATTAT ATGAAGGTAC  1680
TGGAATAAAA GGAACAGACA TCCCTTTCTA ACTGCACTGC CTACATGCGT ATTAAGGTCC  1740
ATTCTGCCTG TGTGTGCTGT GGCTTTGAAC TGTAACACCT CTAATCAATT CAGGAGAAAC  1800
ACATATCATT TAAAGCAACA TAGGCTAACC TGTANGTAAC ACTGCAGTAT TGATGTTTTA  1860
CTGCAAATCT TATGGGTCTA GATAATCAGT AAAAGCCATC TTCCATAGTT GGTGTTAGAA  1920
CATTGCCCTA TTGGT                                                  1935
```

(2) INFORMATION FOR SEQ ID NO:12:

(i) SEQUENCE CHARACTERISTICS:
    (A) LENGTH: 1282 base pairs
    (B) TYPE: nucleic acid
    (C) STRANDEDNESS: single (D) TOPOLOGY: linear (vii) IMMEDIATE SOURCE:
          (A) LIBRARY: PROSNOT06
          (B) CLONE: 827431

(xi) SEQUENCE DESCRIPTION: SEQ ID NO:12:

```
GAAGTTTCTC ACTAGGGTCT TCTCTGGCCC AGCCTTTGAC TGAAGCTGGT CTGGAGACAG      60

GGGCATTAGA GAAGTGACTC ATAGATGGCC TAAAGAAGCG GGGCCACTCA AGGACCCAGG     120

ACAGAGGGAA GAGGGCCAAC CCAGCTGGAC CACAGGCAAA CCCCATTGCC TTTGAGAGAA     180

AGAAGAGGAC CCGGTGAAAC ATGCTGCTGC TGAAGAAACA CACGGAGGAC ATCAGCAGCG     240

TCTACGAGAT CCGCGAGAGG CTCGGCTCGG GTGCCTTCTC CGAGGTGGTG CTGGCCCAGG     300

AGCGGGGCTC CGCACACCTC GTGGCCCTCA AGTGCATCCC CAAGAAGGCC CTCCGGGGCA     360

AGGAGGCCCT GGTGGAGAAC GAGATCGCAG TGCTCCGTAG GATCAGTCAC CCCAACATCG     420

TCGCTCTGGA GGATGTCCAC GAGAGCCCTT CCCACCTCTA CCTGGCCATG GAACTGGTGA     480

CGGGTGGCGA GCTGTTTGAC CGCATCATGG AGCGCGGCTC CTACACAGAG AAGGATGCCA     540

GCCATCTGGT GGGTCAGGTC CTTGGCGCCG TCTCCTACCT GCACAGCCTG GGGATCGTGC     600

ACCGGGACCT CAAGCCCGAA AACCTCCTGT ATGCCACGCC CTTTGAGGAC TCGAAGATCA     660

TGGTCTCTGA CTTTGGACTC TCCAAAATCC AGGCTGGGAA CATGCTAGGC ACCGCCTGTG     720

GGACCCCTGG ATATGTGGCC CCAGAGCTCT TGGAGCAGAA ACCCTACGGG AAGGCCGTAG     780

ATGTGTGGGC CCTGGGCGTC ATCTCCTACA TCCTGCTGTG TGGGTACCCC CCCTTCTACG     840

ACGAGAGCGA CCCTGAGCTC TTCAGCCAGA TCCTGAGGGC CAGCTATGAG TTTGACTNTC     900

CTTTCTGGGA TGACATCTCA GAATCAGGCA AAGACTTTAT TCGGCACCTT CTGGAGCGAG     960

ACCTTCAGAA GAGGTTCACC TGCCAACAGG CCTTGCGGGA CCTTTGGATC TTTTGGGACA    1020

CAGGCTTTGG CAGGGACATC TTAGGGTTTG TCAGTGAGCA GATCCGGAAG AACTTTGCTT    1080

GGACACACTG GAAGCGAGCC TTCAATGCCA CCTTGTTCCT GCGCCACATC CGGAAGCTGG    1140

GGCAGATCCC AGAGGGCGAG GGGGCCTCTG AGCAGGGCAT GGSCCGNCAC AGCCACTNAG    1200

GCCTTCGTGC TGGCCAGCCC CCCAAGTGGT GATGCCCAGG NAGATGCCGA GGCCAAGTGG    1260

ANTGANCCCC AGATTTNCTT NC                                             1282
```

(2) INFORMATION FOR SEQ ID NO:13:

(i) SEQUENCE CHARACTERISTICS:
        (A) LENGTH: 1866 base pairs
        (B) TYPE: nucleic acid
        (C) STRANDEDNESS: single
        (D) TOPOLOGY: linear (vii) IMMEDIATE SOURCE:
          (A) LIBRARY: COLNTUT03
          (B) CLONE: 1340712

(xi) SEQUENCE DESCRIPTION: SEQ ID NO:13:

```
CGGCGGAGGG CGCAGGCGGC TGGGCGCCTG GCGAGTGGAC TGTTCGAGCC CTTCCGCTGG      60

GACCCGGGCC CTGGCTCCGG CCCCGCGATG GGAGCTGCTC TCCGCGGGCT GAGCCTGTCA     120

GCATCCTCGA CGCACCCTGG TCCCTGAAGT CGGAGAAGAG CCCCTACCCA CCCACACCCC     180

CTTGCCCCAT TTTGGGTCGC CTGGGTCCTC AGTCCTAGCG GATCCTCAGT CCTAGCGGCC     240

ACCGGGTCTG AAAGGAGCAA GACGATGATC CTGGCGTCGG TGCTGAGGAG CGGTCCCGGG     300

GGCGGGCTTC CGCTCCGGCC CCTCCTGGGA CCCGCACTCG CGCTCCGGGC CCGCTCGACG     360
```

```
TCGGCCACCG ACACACACCA CGTGGAGATG GCTCGGGAGC GCTCCAAGAC CGTCACCTCC    420

TTTTACAACC AGTCGGCCAT CGACGCGGCA GCGGAGAAGC CCTCAGTCCG CCTAACGCCC    480

ACCATGATGC TCTACGCTGG CCGCTCTCAG GACGGCAGCC ACCTTCTGAA AAGTGCTCGG    540

TACCTGCAGC AAGAACTTCC AGTGAGGATT GCTCACCGCA TCAAGGGCTT CCGCTGCCTT    600

CCTTTCATCA TTGGCTGCAA CCCCACCATA CTGCACGTGC ATGAGCTATA TATCCGTGCC    660

TTCCAGAAGC TGACAGACTT CCCTCCGATC AAGGACCAGG CGGACGAGGC CCAGTACTGC    720

CAGCTGGTGC GACAGCTGCT GGATGACCAC AAGGATGTGG TGACCCTCTT GGCAGAGGGC    780

CTACGTGAGA GCCGGAAGCA CATAGAGGAT GAAAAGCTCG TCCGCTACTT CTTGGACAAG    840

ACGCTGACTT CGAGGCTTGG AATCCGCATG TTGGCCACGC ATCACCTGGC GCTGCATGAG    900

GACAAGCCTG ACTTTGTCGG CATCATCTGT ACTCGTCTCT CACCAAAGAA GATTATTGAG    960

AAGTGGGTGG ACTTTGCCAG ACGCCTGTGT GAGCACAAGT ATGGCAATGC GCCCCGTGTC   1020

CGCATCAATG GCCATGTGGC TGCCCGGTTC CCCTTCATCC CTATGCCACT GGACTACATC   1080

CTGCCGGAGC TGCTCAAGAA TGCCATGAGA GCCACAATGG AGAGCCACCT AGACACTCCC   1140

TACAATGTCC CAGATGTGGT CATCACCATC GCCAACAATG ATGTCGATCT GATCATCAGG   1200

ATCTCAGACC GTGGTGGAGG AATCGCTCAC AAAGATCTGG ACCGGGTCAT GGACTACCAC   1260

TTCACTACTG CTGAGGCCAG CACACAGGAC CCCCGGATCA GCCCCTCTT  TGGCCATCTG   1320

GACATGCATA GTGGCGCCCA GTCAGGACCC ATGCACGGCT TTGGCTTCGG GTTGCCCACG   1380

TCACGGGCCT ACGCGGAGTA CCTCGGTGGG TCTCTGCAGC TGCAGTCCCT GCAGGGCATT   1440

GGCACGGACG TCTACCTGCG GCTCCGCCAC ATCGATGGCC GGGAGGAAAG CTTCCGGATC   1500

TGACCCCACA GCCTTTGGCC TGCTCACCCG ACCAGCCTGG GCCGCATTCC CTGCAGGACC   1560

TCCCGGGTCA GGCAGGGCGG CCCCCTGCTC CACACACTGC TGCATCTTGG GTCTCAGGGA   1620

CCCAGACAGA TGGACTTACA TGGAGCTGGG CACTGCCCCT GCCTCAACAG GGTCCATTGC   1680

TCTCTCGCCT CAGAACTTGG AGCAGGGAAG TGGGCACCTG AGGCCTCAGC ACAGTGTCGT   1740

CATTCTCTTC TGGGGACCC  CACTCTGAGC TGTTATTAAA GTTCACATTT TGGAATGGCC   1800

AGAAAAGAAG GAAGGTGGAT GGTGGTGAGG AGGGGTGGGG AGAGGTGAGG TGGTTGTGGT   1860

TTGTGT                                                              1866

(2) INFORMATION FOR SEQ ID NO:14:

(i) SEQUENCE CHARACTERISTICS:
        (A) LENGTH: 1435 base pairs
        (B) TYPE: nucleic acid
        (C) STRANDEDNESS: single
        (D) TOPOLOGY: linear (vii) IMMEDIATE SOURCE:
        (A) LIBRARY: PENITUT01
        (B) CLONE: 1452972

(xi) SEQUENCE DESCRIPTION: SEQ ID NO:14:

GGCCCCAGCG CTCGGCCGGC CGCGAGCCCG CCGGCCGGGG ACGAGCGTCG CAGCTCATGC     60

TGATCGCTGT CCTCCTCCTC CCCCTCAGGC GGCGCTGGCG GCGGCCCTGG GACCCGCGGA    120

AGCCGGCATG CTGGAGAAGC TGGAGTTCGA GGACGAAGCA GTAGAAGACT CAGAAAGTGG    180

TGTTTACATG CGATTCATGA GGTCACACAA GTGTTATGAC ATCGTTCCAA CCAGTTCAAA    240

GCTTGTTGTC TTTGATACTA CATTACAAGT TAAAAAGGCC TTCTTTGCTT TGGTAGCCAA    300

CGGTGTCCGA GCAGCGCCAC TGTGGGAGAG TAAAAAACAA AGTTTTGTAG GAATGCTAAC    360
```

```
AATTACAGAT TTCATAAATA TACTACATAG ATACTATAAA TCACCTATGG TACAGATTTA      420

TGAATTAGAG GAACATAAAA TTGAAACATG GAGGGAGCTT TATTTACAAG AAACATTTAA      480

GCCTTTAGTG AATATATCTC CAGATGCAAG CCTCTTCGAT GCTGTATACT CCTTGATCAA      540

AAATAAAATC CACAGATTGC CCGTTATTGA CCCTATCAGT GGGAATGCAC TTTATATACT      600

TACCCACAAA AGAATCCTCA AGTTCCTCCA GCTTTTTATG TCTGATATGC CAAAGCCTGC      660

CTTCATGAAG CAGAACCTGG ATGAGCTTGG AATAGGAACG TACCACAACA TTGCCTTCAT      720

ACATCCAGAC ACTCCCATCA TCAAAGCCTT GAACATATTT GTGGAAAGAC GAATATCAGC      780

TCTGCCTGTT GTGGATGAGT CAGGAAAAGT TGTAGATATT TATTCCAAAT TTGATGTAAT      840

TAATCTTGCT GCTGAGAAAA CATACAATAA CCTAGATATC ACGGTGACCC AGGCCCTTCA      900

GCACCGTTCA CAGTATTTTG AAGGTGTTGT GAAGTGCAAT AAGCTGGAAA TACTGGAGAC      960

CATCGTGGAC AGAATAGTAA GAGCTGAGGT CCATCGGCTG GTGGTGGTAA ATGAAGCAGA     1020

TAGTATTGTG GGTATTATTT CCCTGTCGGA CATTCTGCAA GCCCTGATCC TCACACCAGC     1080

AGGTGCCAAA CAAAAGGAGA CAGAAACGGA GTGACCGCCG TGAATGTAGA CGCCCTAGGA     1140

GGAGAACTTG AACAAAGTCT CTGGGTCACG TTTTGCCTCA TGAACACTGG CTGCAAGTGG     1200

TTAAGAATGT ATATCAGGGT TTAACAATAG GTATTTCTTC CAGTGATGTT GAAATTAAGC     1260

TTAAAAAAGA AAGATTTTAT GTGCTTGAAG ATTCAGGCTT GCATTAAAAG ACTGTTTTCA     1320

GACCTTTGTC TGAAGGATTT TAAATGCTGT ATGTCATTAA AGTGCACTGT GTCCTGAAGT     1380

TTTCATTATT TTTCATTTCA AAGAATTCAC TGGTATGGAA CAGGTGATGT GGCAT          1435
```

(2) INFORMATION FOR SEQ ID NO:15:

(i) SEQUENCE CHARACTERISTICS:
        (A) LENGTH: 607 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1827450

(xi) SEQUENCE DESCRIPTION: SEQ ID NO:15:

```
Met Leu Ala Gly Leu Pro Thr Ser Asp Pro Gly Arg Leu Ile Thr Asp
 1               5                  10                  15

Pro Arg Ser Gly Arg Thr Tyr Leu Lys Gly Arg Leu Leu Gly Lys Gly
            20                  25                  30

Gly Phe Ala Arg Cys Tyr Glu Ala Thr Asp Thr Glu Thr Gly Ser Ala
        35                  40                  45

Tyr Ala Val Lys Val Ile Pro Gln Ser Arg Val Ala Lys Pro His Gln
    50                  55                  60

Arg Glu Lys Ile Leu Asn Glu Ile Glu Leu His Arg Asp Leu Gln His
65                  70                  75                  80

Arg His Ile Val Arg Phe Ser His His Phe Glu Asp Ala Asp Asn Ile
                85                  90                  95

Tyr Ile Phe Leu Glu Leu Cys Ser Arg Lys Ser Leu Ala His Ile Trp
            100                 105                 110

Lys Ala Arg His Thr Leu Leu Glu Pro Glu Val Arg Tyr Tyr Leu Arg
        115                 120                 125

Gln Ile Leu Ser Gly Leu Lys Tyr Leu His Gln Arg Gly Ile Leu His
    130                 135                 140

Arg Asp Leu Lys Leu Gly Asn Phe Phe Ile Thr Glu Asn Met Glu Leu
```

```
                145                 150                 155                 160
Lys Val Gly Asp Phe Gly Leu Ala Ala Arg Leu Glu Pro Pro Glu Gln
                    165                 170                 175
Arg Lys Lys Thr Ile Cys Gly Thr Pro Asn Tyr Val Ala Pro Glu Val
                    180                 185                 190
Leu Leu Arg Gln Gly His Gly Pro Glu Ala Asp Val Trp Ser Leu Gly
                    195                 200                 205
Cys Val Met Tyr Thr Leu Leu Cys Gly Ser Pro Pro Phe Glu Thr Ala
                    210                 215                 220
Asp Leu Lys Glu Thr Tyr Arg Cys Ile Lys Gln Val His Tyr Thr Leu
225                 230                 235                 240
Pro Ala Ser Leu Ser Leu Pro Ala Arg Gln Leu Leu Ala Ala Ile Leu
                    245                 250                 255
Arg Ala Ser Pro Arg Asp Arg Pro Ser Ile Asp Gln Ile Leu Arg His
                    260                 265                 270
Asp Phe Phe Thr Lys Gly Tyr Thr Pro Asp Arg Leu Pro Ile Ser Ser
                    275                 280                 285
Cys Val Thr Val Pro Asp Leu Thr Pro Pro Asn Pro Ala Arg Ser Leu
                    290                 295                 300
Phe Ala Lys Val Thr Lys Ser Leu Phe Gly Arg Lys Lys Lys Ser Lys
305                 310                 315                 320
Asn His Ala Gln Glu Arg Asp Glu Val Ser Gly Leu Val Ser Gly Leu
                    325                 330                 335
Met Arg Thr Ser Val Gly His Gln Asp Ala Arg Pro Glu Ala Pro Ala
                    340                 345                 350
Ala Ser Gly Pro Ala Pro Val Ser Leu Val Glu Thr Ala Pro Glu Asp
                    355                 360                 365
Ser Ser Pro Arg Gly Thr Leu Ala Ser Ser Gly Asp Gly Phe Glu Glu
                    370                 375                 380
Gly Leu Thr Val Ala Thr Val Val Glu Ser Ala Leu Cys Ala Leu Arg
385                 390                 395                 400
Asn Cys Ile Ala Phe Met Pro Pro Ala Glu Gln Asn Pro Ala Pro Leu
                    405                 410                 415
Ala Gln Pro Glu Pro Leu Val Trp Val Ser Lys Trp Val Asp Tyr Ser
                    420                 425                 430
Asn Lys Phe Gly Phe Gly Tyr Gln Leu Ser Ser Arg Arg Val Ala Val
                    435                 440                 445
Leu Phe Asn Asp Gly Thr His Met Ala Leu Ser Ala Asn Arg Lys Thr
                    450                 455                 460
Val His Tyr Asn Pro Thr Ser Thr Lys His Phe Ser Phe Ser Val Gly
465                 470                 475                 480
Ala Val Pro Arg Ala Leu Gln Pro Gln Leu Gly Ile Leu Arg Tyr Phe
                    485                 490                 495
Ala Ser Tyr Met Glu Gln His Leu Met Lys Gly Gly Asp Leu Pro Ser
                    500                 505                 510
Val Glu Glu Val Glu Val Pro Ala Pro Pro Leu Leu Leu Gln Trp Val
                    515                 520                 525
Lys Thr Asp Gln Ala Leu Leu Met Leu Phe Ser Asp Gly Thr Val Gln
                    530                 535                 540
Val Asn Phe Tyr Gly Asp His Thr Lys Leu Ile Leu Ser Gly Trp Glu
545                 550                 555                 560
Pro Leu Leu Val Thr Phe Val Ala Arg Asn Arg Ser Ala Cys Thr Tyr
                    565                 570                 575
```

```
Leu Ala Ser His Leu Arg Gln Leu Gly Cys Ser Pro Asp Leu Arg Gln
            580                 585                 590

Arg Leu Arg Tyr Ala Leu Arg Leu Leu Arg Asp Arg Ser Pro Ala
        595                 600                 605
```

(2) INFORMATION FOR SEQ ID NO:16:

(i) SEQUENCE CHARACTERISTICS:
        (A) LENGTH: 396 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1827450

(xi) SEQUENCE DESCRIPTION: SEQ ID NO:16:

```
Met Pro Arg Val Lys Ala Ala Gln Ala Gly Arg Gln Ser Ser Ala Lys
1               5                   10                  15

Arg His Leu Ala Glu Gln Phe Ala Val Gly Glu Ile Ile Thr Asp Met
            20                  25                  30

Ala Lys Lys Glu Trp Lys Val Gly Leu Pro Ile Gly Gln Gly Gly Phe
        35                  40                  45

Gly Cys Ile Tyr Leu Ala Asp Met Asn Ser Ser Glu Ser Val Gly Ser
50                  55                  60

Asp Ala Pro Cys Val Val Lys Val Glu Pro Ser Asp Asn Gly Pro Leu
65                  70                  75                  80

Phe Thr Glu Leu Lys Phe Tyr Gln Arg Ala Ala Lys Pro Glu Gln Ile
                85                  90                  95

Gln Lys Trp Ile Arg Thr Arg Lys Leu Lys Tyr Leu Gly Val Pro Lys
            100                 105                 110

Tyr Trp Gly Ser Gly Leu His Asp Lys Asn Gly Lys Ser Tyr Arg Phe
        115                 120                 125

Met Ile Met Asp Arg Phe Gly Ser Asp Leu Gln Lys Ile Tyr Glu Ala
130                 135                 140

Asn Ala Lys Arg Phe Ser Arg Lys Thr Val Leu Gln Leu Ser Leu Arg
145                 150                 155                 160

Ile Leu Asp Ile Leu Glu Tyr Ile His Glu His Glu Tyr Val His Gly
                165                 170                 175

Asp Ile Lys Ala Ser Asn Leu Leu Leu Asn Tyr Lys Asn Pro Asp Gln
            180                 185                 190

Val Tyr Leu Val Asp Tyr Gly Leu Ala Tyr Arg Tyr Cys Pro Glu Gly
        195                 200                 205

Val His Lys Glu Tyr Lys Glu Asp Pro Lys Arg Cys His Asp Gly Thr
210                 215                 220

Ile Glu Phe Thr Ser Ile Asp Ala His Asn Gly Val Ala Pro Ser Arg
225                 230                 235                 240

Arg Gly Asp Leu Glu Ile Leu Gly Tyr Cys Met Ile Gln Trp Leu Thr
                245                 250                 255

Gly His Leu Pro Trp Glu Asp Asn Leu Lys Asp Pro Lys Tyr Val Arg
            260                 265                 270

Asp Ser Lys Ile Arg Tyr Arg Glu Asn Ile Ala Ser Leu Met Asp Lys
        275                 280                 285

Cys Phe Pro Glu Lys Asn Lys Pro Gly Glu Ile Ala Lys Tyr Met Glu
290                 295                 300
```

-continued

```
Thr Val Lys Leu Leu Asp Tyr Thr Glu Lys Pro Leu Tyr Glu Asn Leu
305                 310                 315                 320

Arg Asp Ile Leu Leu Gln Gly Leu Lys Ala Ile Gly Ser Lys Asp Asp
                325                 330                 335

Gly Lys Leu Asp Leu Ser Val Val Glu Asn Gly Gly Leu Lys Ala Lys
                340                 345                 350

Thr Ile Thr Lys Lys Arg Lys Lys Glu Ile Glu Glu Ser Lys Glu Pro
            355                 360                 365

Gly Val Glu Asp Thr Glu Trp Ser Asn Thr Gln Thr Glu Glu Ala Ile
            370                 375                 380

Gln Thr Arg Ser Arg Thr Arg Lys Arg Val Gln Lys
385                 390                 395
```

(2) INFORMATION FOR SEQ ID NO:17:

(i) SEQUENCE CHARACTERISTICS:
        (A) LENGTH: 400 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 854170

(xi) SEQUENCE DESCRIPTION: SEQ ID NO:17:

```
Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
                20                  25                  30

His Leu Val Asp Leu Gln Lys Lys Leu Glu Glu Leu Asp Leu Asp Glu
            35                  40                  45

Gln Gln Arg Lys Arg Leu Glu Ala Phe Leu Thr Gln Lys Ala Lys Val
        50                  55                  60

Gly Glu Leu Lys Asp Asp Asp Phe Glu Arg Ile Ser Glu Leu Gly Ala
65                  70                  75                  80

Gly Asn Gly Gly Val Val Thr Lys Ala Arg His Arg Pro Ser Gly Leu
                85                  90                  95

Ile Met Ala Arg Lys Leu Ile His Leu Glu Ile Lys Pro Ala Val Arg
                100                 105                 110

Asn Gln Ile Ile Arg Glu Leu Gln Val Leu His Glu Cys Asn Ser Pro
            115                 120                 125

Tyr Ile Val Gly Phe Tyr Gly Ala Phe Tyr Ser Asp Gly Glu Ile Ser
        130                 135                 140

Ile Cys Met Glu His Met Asp Gly Gly Ser Leu Asp Gln Val Leu Lys
145                 150                 155                 160

Glu Ala Lys Arg Ile Pro Glu Asp Ile Leu Gly Lys Val Ser Ile Ala
                165                 170                 175

Val Leu Arg Gly Leu Ala Tyr Leu Arg Glu Lys His Gln Ile Met His
            180                 185                 190

Arg Asp Val Lys Pro Ser Asn Ile Leu Val Asn Ser Arg Gly Glu Ile
        195                 200                 205

Lys Leu Cys Asp Phe Gly Val Ser Gly Gln Leu Ile Asp Ser Met Ala
    210                 215                 220

Asn Ser Phe Val Gly Thr Arg Ser Tyr Met Ser Pro Glu Arg Leu Gln
225                 230                 235                 240

Gly Thr His Tyr Ser Val Gln Ser Asp Ile Trp Ser Met Gly Leu Ser
```

```
                    245                 250                 255
Leu Val Glu Leu Ala Ile Gly Arg Tyr Pro Ile Pro Pro Asp Ala
                260                 265                 270
Lys Glu Leu Glu Ala Ser Phe Gly Arg Pro Val Val Asp Gly Ala Asp
            275                 280                 285
Gly Glu Pro His Ser Val Ser Pro Arg Pro Arg Pro Gly Arg Pro
        290                 295                 300
Ile Ser Gly His Gly Met Asp Ser Arg Pro Ala Met Ala Ile Phe Glu
305                 310                 315                 320
Leu Leu Asp Tyr Ile Val Asn Glu Pro Pro Lys Leu Pro Ser Gly
                325                 330                 335
Val Phe Ser Ser Asp Phe Gln Glu Phe Val Asn Lys Cys Leu Ile Lys
            340                 345                 350
Asn Pro Ala Glu Arg Ala Asp Leu Lys Leu Leu Thr Asn His Ala Phe
        355                 360                 365
Ile Lys Arg Ser Glu Gly Glu Asp Val Asp Phe Ala Gly Trp Leu Cys
        370                 375                 380
Arg Thr Leu Arg Leu Lys Gln Pro Ser Thr Pro Thr Arg Thr Ala Val
385                 390                 395                 400

(2) INFORMATION FOR SEQ ID NO:18:

(i) SEQUENCE CHARACTERISTICS:
        (A) LENGTH: 465 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 8541070

(xi) SEQUENCE DESCRIPTION: SEQ ID NO:18:

Met Ala Met Thr Gly Ser Thr Pro Cys Ser Ser Met Ser Asn His Thr
 1               5                  10                  15
Lys Glu Arg Val Thr Met Thr Lys Val Thr Leu Glu Asn Phe Tyr Ser
                20                  25                  30
Asn Leu Ile Ala Gln His Glu Glu Arg Glu Met Arg Gln Lys Lys Leu
            35                  40                  45
Glu Lys Val Met Glu Glu Gly Leu Lys Asp Glu Glu Lys Arg Leu
        50                  55                  60
Arg Arg Ser Ala His Ala Arg Lys Glu Thr Glu Phe Leu Arg Leu Lys
65                  70                  75                  80
Arg Thr Arg Leu Gly Leu Glu Asp Phe Glu Ser Leu Lys Val Ile Gly
                85                  90                  95
Arg Gly Ala Phe Gly Glu Val Arg Leu Val Gln Lys Lys Asp Thr Gly
            100                 105                 110
His Val Tyr Ala Met Lys Ile Leu Arg Lys Ala Asp Met Leu Glu Lys
        115                 120                 125
Glu Gln Val Gly His Ile Arg Ala Glu Arg Asp Ile Leu Val Glu Ala
        130                 135                 140
Asp Ser Leu Trp Val Val Lys Met Phe Tyr Ser Phe Gln Asp Lys Leu
145                 150                 155                 160
Asn Leu Tyr Leu Ile Met Glu Phe Leu Pro Gly Gly Asp Met Met Thr
                165                 170                 175
Leu Leu Met Lys Lys Asp Thr Leu Thr Glu Glu Glu Thr Gln Phe Tyr
            180                 185                 190
```

```
Ile Ala Glu Thr Val Leu Ala Ile Asp Ser Ile His Gln Leu Gly Phe
        195                 200                 205
Ile His Arg Asp Ile Lys Pro Asp Asn Leu Leu Asp Ser Lys Gly
        210                 215                 220
His Val Lys Leu Ser Asp Phe Gly Leu Cys Thr Gly Leu Lys Lys Ala
225                 230                 235                 240
His Arg Thr Glu Phe Tyr Arg Asn Leu Asn His Ser Leu Pro Ser Asp
                245                 250                 255
Phe Thr Phe Gln Asn Met Asn Ser Lys Arg Lys Ala Glu Thr Trp Lys
                260                 265                 270
Arg Asn Arg Arg Gln Leu Ala Phe Ser Thr Val Gly Thr Pro Asp Tyr
        275                 280                 285
Ile Ala Pro Glu Val Phe Met Gln Thr Gly Tyr Asn Lys Leu Cys Asp
        290                 295                 300
Trp Trp Ser Leu Gly Val Ile Met Tyr Glu Met Leu Ile Gly Tyr Pro
305                 310                 315                 320
Pro Phe Cys Ser Glu Thr Pro Gln Glu Thr Tyr Lys Lys Val Met Asn
                325                 330                 335
Trp Lys Glu Thr Leu Thr Phe Pro Pro Glu Val Pro Ile Ser Glu Lys
                340                 345                 350
Ala Lys Asp Leu Ile Leu Arg Phe Cys Cys Glu Trp Glu His Arg Ile
                355                 360                 365
Gly Ala Pro Gly Val Glu Glu Ile Lys Ser Asn Ser Phe Phe Glu Gly
        370                 375                 380
Val Asp Trp Glu His Ile Arg Glu Arg Pro Ala Ala Ile Ser Ile Glu
385                 390                 395                 400
Ile Lys Ser Ile Asp Asp Thr Ser Asn Phe Asp Glu Phe Pro Glu Ser
                405                 410                 415
Asp Ile Leu Lys Pro Thr Val Ala Thr Ser Asn His Pro Glu Thr Asp
                420                 425                 430
Tyr Lys Asn Lys Asp Trp Val Phe Ile Asn Tyr Thr Tyr Lys Arg Phe
                435                 440                 445
Glu Gly Leu Thr Ala Arg Gly Ala Ile Pro Ser Tyr Met Lys Ala Ala
        450                 455                 460
Lys
465

(2) INFORMATION FOR SEQ ID NO:19:

(i) SEQUENCE CHARACTERISTICS:
        (A) LENGTH: 370 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 790790

(xi) SEQUENCE DESCRIPTION: SEQ ID NO:19:

Met Leu Gly Ala Val Glu Gly Pro Arg Trp Lys Gln Ala Glu Asp Ile
1               5                   10                  15
Arg Asp Ile Tyr Asp Phe Arg Asp Val Leu Gly Thr Gly Ala Phe Ser
                20                  25                  30
Glu Val Ile Leu Ala Glu Asp Lys Arg Thr Gln Lys Leu Val Ala Ile
        35                  40                  45
```

```
Lys Cys Ile Ala Lys Glu Ala Leu Glu Gly Lys Glu Gly Ser Met Glu
 50                  55                  60

Asn Glu Ile Ala Val Leu His Lys Ile Lys His Pro Asn Ile Val Ala
 65                      70                  75                  80

Leu Asp Asp Ile Tyr Glu Ser Gly Gly His Leu Tyr Leu Ile Met Gln
                     85                  90                  95

Leu Val Ser Gly Gly Glu Leu Phe Asp Arg Ile Val Glu Lys Gly Phe
                100                 105                 110

Tyr Thr Glu Arg Asp Ala Ser Arg Leu Ile Phe Gln Val Leu Asp Ala
        115                 120                 125

Val Lys Tyr Leu His Asp Leu Gly Ile Val His Arg Asp Leu Lys Pro
    130                 135                 140

Glu Asn Leu Leu Tyr Tyr Ser Leu Asp Glu Asp Ser Lys Ile Met Ile
145                 150                 155                 160

Ser Asp Phe Gly Leu Ser Lys Met Glu Asp Pro Gly Ser Val Leu Ser
                165                 170                 175

Thr Ala Cys Gly Thr Pro Gly Tyr Val Ala Pro Glu Val Leu Ala Gln
                180                 185                 190

Lys Pro Tyr Ser Lys Ala Val Asp Cys Trp Ser Ile Gly Val Ile Ala
                195                 200                 205

Tyr Ile Leu Leu Cys Gly Tyr Pro Pro Phe Tyr Asp Glu Asn Asp Ala
210                 215                 220

Lys Leu Phe Glu Gln Ile Leu Lys Ala Glu Tyr Glu Phe Asp Ser Pro
225                 230                 235                 240

Tyr Trp Asp Asp Ile Ser Asp Ser Ala Lys Asp Phe Ile Arg His Leu
                245                 250                 255

Met Glu Lys Asp Pro Glu Lys Arg Phe Thr Cys Glu Gln Ala Leu Gln
                260                 265                 270

His Pro Trp Ile Ala Gly Asp Thr Ala Leu Asp Lys Asn Ile His Gln
            275                 280                 285

Ser Val Ser Glu Gln Ile Lys Lys Asn Phe Ala Lys Ser Lys Trp Lys
    290                 295                 300

Gln Ala Phe Asn Ala Thr Ala Val Val Arg His Met Arg Lys Leu Gln
305                 310                 315                 320

Leu Gly Thr Ser Gln Glu Gly Gln Gln Thr Ala Ser His Gly Glu
                325                 330                 335

Leu Leu Thr Pro Val Ala Gly Gly Pro Ala Ala Gly Cys Cys Cys Arg
                340                 345                 350

Asp Cys Cys Val Glu Pro Gly Thr Glu Leu Ser Pro Thr Leu Pro His
                355                 360                 365

Gln Leu
    370

(2) INFORMATION FOR SEQ ID NO:20:

(i) SEQUENCE CHARACTERISTICS:
        (A) LENGTH: 382 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 924921

(xi) SEQUENCE DESCRIPTION: SEQ ID NO:20:

Ser Thr Ser Ala Thr Asp Thr His His Val Glu Leu Ala Arg Glu Arg
```

```
                1               5                    10                   15
    Ser Lys Thr Val Thr Ser Phe Tyr Asn Gln Ser Ala Ile Asp Val Val
                    20                   25                  30

Ala Glu Lys Pro Ser Val Arg Leu Thr Pro Thr Met Met Leu Tyr Ser
                35                  40                  45

Gly Arg Ser Gln Asp Gly Ser His Leu Leu Lys Ser Gly Arg Tyr Leu
            50                  55                  60

Gln Gln Glu Leu Pro Val Arg Ile Ala His Arg Ile Lys Gly Phe Arg
    65                  70                  75                  80

Ser Leu Pro Phe Ile Ile Gly Cys Asn Pro Thr Ile Leu His Val His
                        85                  90                  95

Glu Leu Tyr Ile Arg Ala Phe Gln Lys Leu Thr Asp Phe Pro Pro Ile
                    100                 105                 110

Lys Asp Gln Ala Asp Glu Ala Gln Tyr Cys Gln Leu Val Arg Gln Leu
                115                 120                 125

Leu Asp Asp His Lys Asp Val Val Thr Leu Leu Ala Glu Gly Leu Arg
                130                 135                 140

Glu Ser Arg Lys His Ile Glu Asp Glu Lys Leu Val Arg Tyr Phe Leu
    145                 150                 155                 160

Asp Lys Thr Leu Thr Ser Arg Leu Gly Ile Arg Met Leu Ala Thr His
                    165                 170                 175

His Leu Ala Leu His Glu Asp Lys Pro Asp Phe Val Gly Ile Ile Cys
                    180                 185                 190

Thr Arg Leu Ser Pro Lys Lys Ile Ile Glu Lys Trp Val Asp Phe Ala
                195                 200                 205

Arg Arg Leu Cys Glu His Lys Tyr Gly Asn Ala Pro Arg Val Arg Ile
    210                 215                 220

Asn Gly His Val Ala Ala Arg Phe Pro Phe Ile Pro Met Pro Leu Asp
    225                 230                 235                 240

Tyr Ile Leu Pro Glu Leu Leu Lys Asn Ala Met Arg Ala Thr Met Glu
                    245                 250                 255

Ser His Leu Asp Thr Pro Tyr Asn Val Pro Asp Val Val Ile Thr Ile
                    260                 265                 270

Ala Asn Asn Asp Val Asp Leu Ile Ile Arg Ile Ser Asp Arg Gly Gly
                275                 280                 285

Gly Ile Ala His Lys Asp Leu Asp Arg Val Met Asp Tyr His Phe Thr
            290                 295                 300

Thr Ala Glu Ala Ser Thr Gln Asp Pro Arg Ile Ser Pro Leu Phe Gly
    305                 310                 315                 320

His Leu Asp Met His Ser Gly Gly Gln Ser Gly Pro Met His Gly Phe
                    325                 330                 335

Gly Phe Gly Leu Pro Thr Ser Arg Ala Tyr Ala Glu Tyr Leu Gly Gly
                340                 345                 350

Ser Leu Gln Leu Gln Ser Leu Gln Gly Ile Gly Thr Asp Val Tyr Leu
                355                 360                 365

Arg Leu Arg His Ile Asp Gly Arg Glu Glu Ser Phe Arg Ile
    370                 375                 380
```

(2) INFORMATION FOR SEQ ID NO:21:

(i) SEQUENCE CHARACTERISTICS:
        (A) LENGTH: 331 amino acids
        (B) TYPE: amino acid
        (C) STRANDEDNESS: single
        (D) TOPOLOGY: linear (vii) IMMEDIATE SOURCE:
      (A) LIBRARY: GenBank
      (B) CLONE: 1335856

(xi) SEQUENCE DESCRIPTION: SEQ ID NO:21:

```
Met Glu Thr Val Ile Ser Ser Asp Ser Ser Pro Ala Val Glu Asn Glu
1               5                   10                  15

His Pro Gln Glu Thr Pro Glu Ser Asn Asn Ser Val Tyr Thr Ser Phe
            20                  25                  30

Met Lys Ser His Arg Cys Tyr Asp Leu Ile Pro Thr Ser Ser Lys Leu
        35                  40                  45

Val Val Phe Asp Thr Ser Leu Gln Val Lys Ala Phe Phe Ala Leu
    50                  55                  60

Val Thr Asn Gly Val Arg Ala Ala Pro Leu Trp Asp Ser Lys Lys Gln
65                  70                  75                  80

Ser Phe Val Gly Met Leu Thr Ile Thr Asp Phe Ile Asn Ile Leu His
                85                  90                  95

Arg Tyr Tyr Lys Ser Ala Leu Val Gln Ile Tyr Glu Leu Glu Glu His
            100                 105                 110

Lys Ile Glu Thr Trp Arg Glu Val Tyr Leu Gln Asp Ser Phe Lys Pro
        115                 120                 125

Leu Val Cys Ile Ser Pro Asn Ala Ser Leu Phe Asp Ala Val Ser Ser
    130                 135                 140

Leu Ile Arg Asn Lys Ile His Arg Leu Pro Val Ile Asp Pro Glu Ser
145                 150                 155                 160

Gly Asn Thr Leu Tyr Ile Leu Thr His Lys Arg Ile Leu Lys Phe Leu
                165                 170                 175

Lys Leu Phe Ile Thr Glu Phe Pro Lys Pro Glu Phe Met Ser Lys Ser
            180                 185                 190

Leu Glu Glu Leu Gln Ile Gly Thr Tyr Ala Asn Ile Ala Met Val Arg
        195                 200                 205

Thr Thr Thr Pro Val Tyr Val Ala Leu Gly Ile Phe Val Gln His Arg
    210                 215                 220

Val Ser Ala Leu Pro Val Val Asp Glu Lys Gly Arg Val Val Asp Ile
225                 230                 235                 240

Tyr Ser Lys Phe Asp Val Ile Asn Leu Ala Ala Glu Lys Thr Tyr Asn
                245                 250                 255

Asn Leu Asp Val Ser Val Thr Lys Ala Leu Gln His Arg Ser His Tyr
            260                 265                 270

Phe Glu Gly Val Leu Lys Cys Tyr Leu His Glu Thr Leu Glu Thr Ile
        275                 280                 285

Ile Asn Arg Leu Val Glu Ala Glu Val His Arg Leu Val Val Val Asp
    290                 295                 300

Glu Asn Asp Val Val Lys Gly Ile Val Ser Leu Ser Asp Ile Leu Gln
305                 310                 315                 320

Ala Leu Val Leu Thr Gly Gly Glu Lys Lys Pro
                325                 330
```